United States Patent [19]

Goodman et al.

[11] Patent Number: 4,975,374

[45] Date of Patent: Dec. 4, 1990

[54] EXPRESSION OF WILD TYPE AND MUTANT GLUTAMINE SYNTHETASE IN FOREIGN HOSTS

[75] Inventors: Howard Goodman, Newton; Shiladitya DasSarma, Amherst, both of Mass.; Edmund Tischer, Palo Alto, Calif.; Theresa K. Peterman, Cambridge, Mass.

[73] Assignee: The General Hospital Corporation, Boston, Mass.

[21] Appl. No.: 10,612

[22] Filed: Feb. 4, 1987

[51] Int. Cl.$^5$ .................. C12N 15/00; C12N 9/00; C12N 1/20; C07H 15/12

[52] U.S. Cl. .................. 435/172.3; 435/183; 435/252.3; 435/252.33; 435/320; 536/27; 935/14; 935/29; 935/30; 935/73

[58] Field of Search .............. 435/183, 240.46, 252.33, 435/320; 536/27; 935/14

[56] References Cited

U.S. PATENT DOCUMENTS 4,594,323  6/1986  Csonka et al. .................. 435/107

FOREIGN PATENT DOCUMENTS

86/02097  4/1986  PCT Int'l Appl. .................. 19/34

OTHER PUBLICATIONS

Tingey, S. V. et al., *EMBO J.* 6:1–9 (1987).
Tingsey, S. V. et al., *Plant Physiol.* 84:366–373 (1987).
Gebhardt, C. et al., *EMBO J.* 5:1429–1435 (1986).
DasSarma et al., *Science* 232:1242–1244 (1986).
Cullimore et al., *J. Mol. Appl. Gen.* 2:589–599 (1984).
Donn et al., *J. Mol. Appl. Gen.* 2:621–635 (1984).
Scolnik et al., *J. Bacteriol.* 155:180–185 (1983).
Fisher et al., *Proc. Natl. Acad. Sci. U.S.A.* 78:3393–3397 (1981).
Sanders et al., *EMBO J.* 3:65–71 (1984).
Young et al., *J. Biol. Chem.* 258:11260–11266 (1983).
Miller et al., *J. Biol. Chem.* 256:11307–11312 (1981).
Leason et al., *Phytochem.* 21:855–857 (1982).
Lara et al., *Plant Physiol.* 76:1019–1023 (1984).
Tingey et al., *EMBO J.* 6:1–9 (1987).
Botstein et al., *Science* 229:1193–1201 (1985).
Coulondre et al., *J. Mol. Biol.* 117:525–575 (1977).
European Search Report for Corresponding Application EPO 87103936.

*Primary Examiner*—Thomas D. Mays
*Attorney, Agent, or Firm*—Saidman, Sterne, Kessler & Goldstein

[57] ABSTRACT

The invention relates to a mutant glutamine synthetase (GS) enzyme which is resistant to inhibition by herbicidal GS inhibitors, such as phosphinothricin (PPT), genetic sequences coding therefor, plants cells and prokaryotes transformed with the genetic sequences, and herbicidal GS inhibitor-resistant plant cells and plants.

30 Claims, 12 Drawing Sheets

Fig. I

FIG. 2
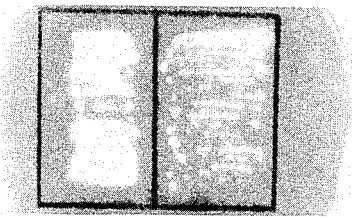
+GLN
A  B
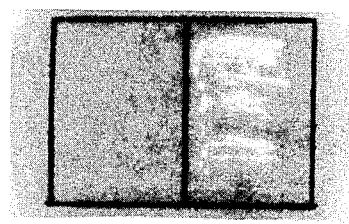
−GLN
A  B

```
                                                  - 35 .
-120  GCGCCGACATCATAACGGTTCTGGCAAATATTCTGAAATGAGCTGTTGACAATTAATCAT

- 10                                    SD .  SalI
      CGGCTCGTATAATGTGTGGAATTGTGAGCGGATAACAATTTCACACAGGAAACAGTCGAC

↑ pCGS1 (+)
   1  ATGTCTCTCCTTTCAGATCTTATCAACCTTGACCTCTCCGAAACCACCGAGAAAATCATC
   1   M  S  L  L  S  D  L  I  N  L  D  L  S  E  T  T  E  K  I  I

GCCGAATACATATGGATTGGTGGATCTGGTTTGGACTTGAGGAGCAAAGCAAGGACTCTA
       A  E  Y  I  W  I  G  G  S  G  L  D  L  R  S  K  A  R  T  L

121  CCAGGACCAGTTACTGACCCTTCACAGCTTCCCAAGTGGAACTATGATGGTTCCAGCACA
  41   P  G  P  V  T  D  P  S  Q  L  P  K  W  N  Y  D  G  S  S  T

GGTCAAGCTCCTGGAGAAGATAGTGAAGTTATTATCTACCCACAAGCCATTTTCAAGGAC
       G  Q  A  P  G  E  D  S  E  V  I  I  Y  P  Q  A  I  F  K  D

241  CCATTTAGAAGGGGTAACAATATCTTGGTTATGTGTGATGCATACACTCCAGCTGGAGAG
  81   P  F  R  R  G  N  N  I  L  V  M  C  D  A  Y  T  P  A  G  E

CCCATTCCCACCAACAAGAGACATGCAGCTGCCAAGATTTTCAGCCATCCTGATGTTGTT
       P  I  P  T  N  K  R  H  A  A  A  K  I  F  S  H  P  D  V  V

NcoI
 361  GCTGAAGTACCATGGTATGGTATTGAGCAAGAATACACCTTGTTGCAGAAAGACATCAAT
 161   A  E  V  P  W  Y  G  I  E  Q  E  Y  T  L  L  Q  K  D  I  N

TGGCCTCTTGGTTGGCCAGTTGGTGGTTTTCCTGGACCTCAGGGACCATACTATTGTGGA
       W  P  L  G  W  P  V  G  G  F  P  G  P  Q  G  P  Y  Y  C  G

481  GCTGGTGCTGACAAGGCATTTGGCCGTGACATTGTTGACTCACATTACAAAGCCTGTCTT
 181   A  G  A  D  K  A  F  G  R  D  I  V  D  S  H  Y  K  A  C  L

EcoRI.
      TATGCCGGCATCAACATCAGTGGAATCAATGGTGAAGTGATGCCTGGTCAATGGGAATTC
       Y  A  G  I  N  I  S  G  I  N  G  E  V  M  P  G  Q  W  E  F
```

FIG. 6

T Val207 (±, formic)

```
601 CAAGTTGGTCCCTCAGTTGGTATCTCTGCTGGTGATGAGATATGGGTTGCTCGTTACATT
201  Q  V  G  P  S  V  G  I  S  A  G  D  E  I  W  V  A  R  Y  I

TTGGAGAGGATCACTGAGGTTGCTGGTGTGGTGCTTTCCTTTGACCCAAAACCAATTAAG
     L  E  R  I  T  E  V  A  G  V  V  L  S  F  D  P  K  P  I  K
```

PPTr T Cys245 (oligo 245.2)
PPTr C Arg245 (oligo 245.2)
PPTr A Ser245 (oligo 245.1)
PPTr A Ser245 (*)   A Gln249  (+, oligo SD17.1)

```
721 GGTGATTGGAATGGTGCTGGTGCTCACACAAATTACAGCACCAAGTCTATGAGAGAAGAT
241  G  D  W  N  G  A  G  A  H  T  N  Y  S  T  K  S  M  R  E  D

. HindIII  .
    GGTGGCTATGAAGTCATCTTGAAAGCAATTGAGAAGCTTGGGAAGAAGCACAAGGAGCAC
     G  G  Y  E  V  I  L  K  A  I  E  K  L  G  K  K  H  K  E  H 841 ATTGCTGCTTATGGAGAAGGCAACGAGCGTAGATTGACAGGGCGACATGAGACAGCTGAC
281  I  A  A  Y  G  E  G  N  E  R  R  L  T  G  R  H  E  T  A  D ATTAACACCTTCTTATGGGGTGTTGCAAACCGTGGTGCGTCGATTAGAGTTGGAAGGGAC
     I  N  T  F  L  W  G  V  A  N  R  G  A  S  I  R  V  G  R  D PPTʳ A Lys332 (*)
                                .           . BamHI .
961 ACAGAGAAAGCAGGGAAAGGTTATTTCGAGGATAGGAGGCCATCATCTAACATGGATCCA
321  T  E  K  A  G  K  G  Y  F  E  D  R  R  P  S  S  N  M  D  P
```

A   pCGS315.2 (-, oligo SD15.2)

```
    TATGTTGTTACTTCCATGATTGCAGACACCACCATTCTCTGGAAACCATAAGCCACCACA
     Y  V  V  T  S  M  I  A  D  T  T  I  L  W  K  P  *

1081 CACACATGCATTGAAGTATTTGAAAGTCATTGTTGATTCCGCATTAGAATTTGGTCATTG

TTTTTTCTAGGATTTGGATTTGTGTTATTGTTATGGTTCACACTTTGTTTGTTTGAATTT

StuI
1201 GAGGCCTCTGCCTCGCGC  1218
```

FIG. 6 (cont.)

PARTIAL SEQUENCES OF THE ROOT-SPECIFIC cDNA CLONE FROM ARABIDOPSIS
AtcGS11

A.
```
  1  TGCTAAAGCT GCTGAGATCT TCAGTAACAA GAAGGTCTCT GGCAGGTTCC
 51  ATGGTTCGGC ATTGAACAAG AGTACACTTT ACTTCAGCAA AACGTCAAAT
101  GGCCTTTAGG TTGGCCTGTT GGAGCGTTCC CTGGTCCTCA GGGTCCTTAC
151  TACTGTGGAG TTGGAGCTGA CAAGATTTGG GGCGTGACAT TTCAGATGCT
```

B.
```
  1  ATTCCGCAAA TCTTTTGGCA GAGATGTTGT TGATTCTCAC TACAAGGCCT
 51  GCTTATACGC TGGGATCAAC ATTAGTGGCC ATCAATGGAG AAGTCATGCC
101  GGGTCAGTGG GAGTTCCAGG TCGGTCCAGC TGTTGGTATC TCGGCTGCTG
151  ATGAAATTTG GGTCGCTCGT TACATTTTGG AGAGGATCAA GAGATTGCTG
201  GTGTAGTGGT ATCTTTTACC C
```

C.
```
  1  TTTAAAATTA GTCGAAACTT TCATGAATCT GATGAACACA CGTGTCTATG
 51  TGGTCTCTCA AGTTGTTTAA ACATTCGGAT TAAGACATTG TTTGTTGTCT
101  TTTCATTTGC ATTTTTAAAA CTCAGAATTG TATGGACAAT GTTCACGGAA
151  TTCGTAATCA TGGTCATAGC TGTTTCCTGT GTGAAATTGT TATCCGCTCA
201  CA
```

FIG. 8

PARTIAL SEQUENCES OF THE ROOT-SPECIFIC cDNA CLONE FROM ARABIDOPSIS
AtcGSr1

A.
1   GCAAATCTTT TGGCAGAGAT GTTGTTGATT CTCACTACAA GGCCTGCTTA
51  TACGCTGGGA TCAACATTAG TGGCCATCAA TGGAGAAGTC ATGCCGGGTC
101 AGTGGGAGTT CCAGGTCGGT CCAGCTGTTG GTATCTCGGC TGCTGATGAA
151 ATTTGGGTCG CTCGTTACAT TTTGGAGAGG ATCCA

B.
1   GATCCTTACA TTGTCATTCC ATGATTGCAG AGACTACAAT CCTCTGGAAT
51  CCTTGATGAT CATCAGATCA AGAAAAAATC TTGAATGTCA CTCAAATTTG
101 TGTTTCTTGC AAGATTCAAA GTTTGTGTTC TCTATCAAGC AATGTCTTAG
151 GATAAGTCAA AGATTTGCTC TGCTTATTCT GCTTTTTATT TACT

FIG. 11

PARTIAL SEQUENCES OF THE ROOT-SPECIFIC cDNA CLONE FROM ARABIDOPSIS
AtcGSr2

A.
```
  1  GGTCGGTATC TCAGCTGCTG ATGAAATATG GATCGCTCGT TACATTTTGG
 51  AGAGGATCAC AGAGATTGCT GGTGTGGTTG TATCTTTTGA CCCAAAACCT
101  ATTCCTGGTG ACTGGAATGG AGCTGGTGCT CACACCAATT ACAGTACTAA
151  ATCAATGAGG GAAGAAGGAG GATACGAGAT AATCGAAGAA GGCGATCGAG
201  AAGCCTGGCT TGAGACACAA GGACACATTT CCGCTTACGG TGAAGGAAAC
251  GAGCGTCGTC TCACGGGACA CCATGAAACT GCTGACATCA ACATTTCCTT
301  TAGGGTGTTG CG
```

B.
```
  1  ATGTGTATTA AGCAATTGTA CCGTTGACAC TGCCGAGTTG TCGATTTGGG
 51  GCCTTTCTTT CTTTTTCTTC TTTTTCATAA TCTTTTGGGT TCTGTGGTTA
101  GAGCAAATTC GGTTTGCTTT GTTTGTTTGA CCTTTATTGA AACCTTTGTA
151  TTGGTACTAA TAATACAATC TAAAAGGCCC
```

FIG. 12

EXPRESSION OF WILD TYPE AND MUTANT GLUTAMINE SYNTHETASE IN FOREIGN HOSTS

The present application is a continuation-in-part of application Ser. No. 906,984 filed Sept. 15, 1986, now abandoned and of application Ser. No. 840,744 filed Mar. 18, 1986 now abandoned.

BACKGROUND OF THE INVENTION

1. Field of the Invention

The present invention relates to the use of recombinant DNA technology for the transformation of hosts such as bacteria or plant cells with genetic sequences for the expression of glutamine synthetase (GS). Genes for both the wild type and GS inhibitor resistant enzymes are disclosed.

2. BRIEF DESCRIPTION OF THE BACKGROUND ART

Genetic and molecular biology methods have been used successfully to address various biochemical questions. They have been used, for example, in selecting for increased catalytic activity or altered inducer binding effects in proteins, by systematic amino acid replacement (Oho, et al., *Science,* 229: 389, 1985; Garges et al., *Cell,* 41: 745, 1985; Miller, N. *The Operon,* Miller *et al. Eds., Cold Spring Harbor,* 1978). However, in general, these studies have been limited to bacterial proteins. The expression of functionally active eukaryotic proteins in prokaryotes should facilitate the structure-function analysis of eukaryotic proteins by the application of many of these techniques, particularly when genetic complementation is feasible.

A particularly interesting enzyme for protein engineering and structure-function analysis is glutamine synthetase (GS) from plants (Miflin et al., in *The Biochemistry of Plants: Amino Acids and Derivatives* Miflin Ed., Vol. 5, P. 169, Academic Press, 1980). GS, together with glutamate synthase, carries out assimilation of ammonia resulting from molecular nitrogen fixation, nitrate reduction, and catabolism. This enzyme is an octamer with a cube-like shape and usually is composed of a single polypeptide. The production of GS appears to be under both genetic and allosteric regulation.

Several herbicides function by inhibiting plant glutamine synthetase. A typical example of such compounds is the glutamic acid analogue, phosphinothricin (PPT). Unfortunately, many of these herbicides inhibit glutamine synthetase present in the crop plants as well as in weeds, thereby limiting the use of such compounds as PPT.

Since herbicidal selectivity is quite crucial in any commercially useful herbicide, it would be of great interest to be able to confer resistance in selected plants to such non-selective herbicides as PPT, as well as to other GS inhibitors.

There is some precedent for the existence of glutamine synthetases resistant to other compounds. It is known that methione sulfoximine (MSO), another glutamate analog, is a mixed competitive inhibitor ($K_i$ of 0.16 mM) of pea leaf glutamine synthetase (Leason *et al., Phytochemistry,* 21: 855, (1982)). Miller et al., (*Journal of Biological Chemistry,* 256: 11307, 1981) studied the properties of several mutants of *Salmonella* resistant to MSO. In one instance, a mutation occurred which apparently altered the bacterial glutamine synthetase at the ammonia binding domain to confer MSO resistance. More recently, Young et al., (ibid, 258: 11260, 1983) reported that mouse 3T6 cells grown in the presence of MSO developed resistance to this compound. The MSO resistant cells had mRNA enriched for glutamine synthetase, and the authors suggested that this finding implied an amplification of the gene. See also, Sanders et al., *Embo Journal,* 3: 65 (1984). Neither the Miller, Young nor Sanders studies reported on plant GS.

PPT-resistant alfalfa cells have recently been reported (Newmark, *Nature,* 305: 383-384, 1983). However, the resistance was due to amplification of the GS gene rather than a specific structural mutation in the GS enzyme expressed. (Donn et al., *Journal of Molecular and Applied Genetics,* 2: 621-635, 1984).

It would therefore be desirable to develop a bacterial strain which contains the genetic sequence for plant glutamine synthetase. One application of this strain would be for the production of increased levels of GS for commercial or industrial purposes. Another application would be in the development of structural mutants which produce biochemically functional plant glutamine synthetase resistant to the action of GS inhibitors.

Once such a structural GS mutant was developed, its gene could be transformed into plant cells and into plants to provide GS inhibitor-resistant plant cells and plants.

SUMMARY OF THE INVENTION

The present invention relates to organisms transformed with a recombinant DNA molecule comprising a sequence coding for glutamine synthetase.

The GS genetic sequences are of two distinct types. A first type of genetic sequence (hereinafter "wild type GS") codes for wild type GS and originates in eukaryotic donors, such as plant cells, e.g., alfalfa. The GS coded thereby is sensitive to herbicidal GS inhibitors such as PPT.

A second type of genetic sequence (hereinafter "mutant GS") codes for a structural mutant of GS and can originate either in prokaryotic or eukaryotic donors, including the eukaryotes mentioned above, or prokaryotes such as bacteria. The GS coded thereby is resistant to inhibition by herbicidal GS inhibitors, such as PPT.

The inventors have discovered that a bacterial mutant of *E. coli,* which is incapable of coding for bacterial glutamine synthetase, can be transformed with the eukaryotic genetic sequence coding for wild type glutamine synthetase, and that the enzyme can be expressed therein.

These *E. coli* transformants can also be subjected to mutagenesis techniques, and made to yield a variety of structural mutant GS enzymes. The sequences for some of these mutant GS genes also complement the *E. coli* hosts, and express therein. More importantly, an understanding of the sequence peculiarities of the mutant genes forms the basis for the preparation of other mutant GS genetic sequences, whether from other eukaryotes than those used as the original source, or from prokaryotic sources.

One embodiment of the invention is based on expressing eukaryotic glutamine synthetase in a prokaryotic cell which, prior to transformation, is incapable of producing its own glutamine synthetase. The host prokaryotic strain is preferably a mutant which, unlike the wild-type prokaryotic strain, cannot produce functional prokaryotic glutamine synthetase or has a level of glutamine synthetase activity lower than that of the wild-type strain. Thus, when such a prokaryotic mutant is transformed according to the invention, the mutant bacterium regains the ability to produce functional glutamine synthetase and is thus capable of growing on media lacking glutamine. The restoration of the ability of the mutant strain to produce a functional substance at useful levels, normally produced by the wild-type strain, is known as complementation.

Thus, the present invention allows the fusion of a plant wild type GS gene to bacterial transcription and translation signals. This fusion enables the genetic complementation of bacterial mutants. This embodiment of the invention represents the first example of complementation in bacteria using a plant gene. The plant enzyme is folded and assembled into an essentially native conformation in the host bacteria. Hence, the invention allows the generation of a system wherein the methods of random and directed mutagenesis (Botstein et al., *Science,* 229:1193, 1985) and bacterial genetics can be used for the structure-function study of plant enzymes. In addition, the present invention allows for the direct selection in *E. coli* for a herbicidal GS inhibitor (e.g., L-phosphinothricin)-resistant glutamine synthetase gene which is useful in the development of herbicide resistant plants.

In another embodiment of the invention then, the mutant GS genetic sequences (which code for herbicidal GS inhibitor resistant enzymes) are placed in recombinant DNA (rDNA) molecules operably linked to a transcription promoter which is operable in plant cells, and the rDNA molecules are used to transform plant cells. The resulting plant cells, plants regenerated therefrom, progeny thereof and their seeds, all carrying and expressing the mutant GS gene, are also part of this invention.

DESCRIPTION OF THE FIGURES

FIG. 2 shows the genetic complementation of an *E. coli* mutant incapable of producing GS, with an engineered alfalfa wild type GS gene. The Petri dish on the left contains minimal M9 medium supplemented with glutamine (+GLN), whereas the growth medium on the right does not contain glutamine (−GLN). Organism A is a mutant strain of *E. coli* incapable of producing a functional glutamine synthetase enzyme. Therefore, it is unable to grow on the media lacking glutamine. Organism B is the same strain of *E. coli* as Organism A after transformation with plasmid pCGS2. Unlike Organism A, Organism B is now able to grow on media with or without exogenously supplied glutamine due to its ability to produce glutamine synthetase.

FIG. 6 contains the complete nucleotide and amino acid sequence of wild type GS, transcription and translation signals of ptac12 (−35, −10, SD), and hexanucleotide restriction sites, as well as several structural variants as follows: delta CGS1, lacking the normal N terminal amino acid residues #2-5, SLLS; GS (val 207); GS (ser 245); GS(gln 249); and delta pCGS315.2. (Glutamine synthetase activity is lost in delta pCGS315.2, which lacks 16 amino acid residues of the carboxyl terminal end.) GS (ser 245), GS (arg 245), GS (lys 245), and GS (lys 332) are PPT resistant mutants.

The standard abreviations for amino acids are used: A, alanine; R, arginine; N, asparagine; D, aspartic acid; C, cysteine; Q, glutamine; E, glutamic acid; G, glycine; H, histidine; I, isoleucine; L, leucine; K, lysine; M, methionine; F, phenylalanine; P, proline; S, serine; T, threonine; W, tryptophan; Y, tyrosine; V, valine. The standard abreviations for deoxyribonucleic acids are used: A, adenine; G, guanine; U, uracil; T, thymine; C, cytosine.

Figure 7:
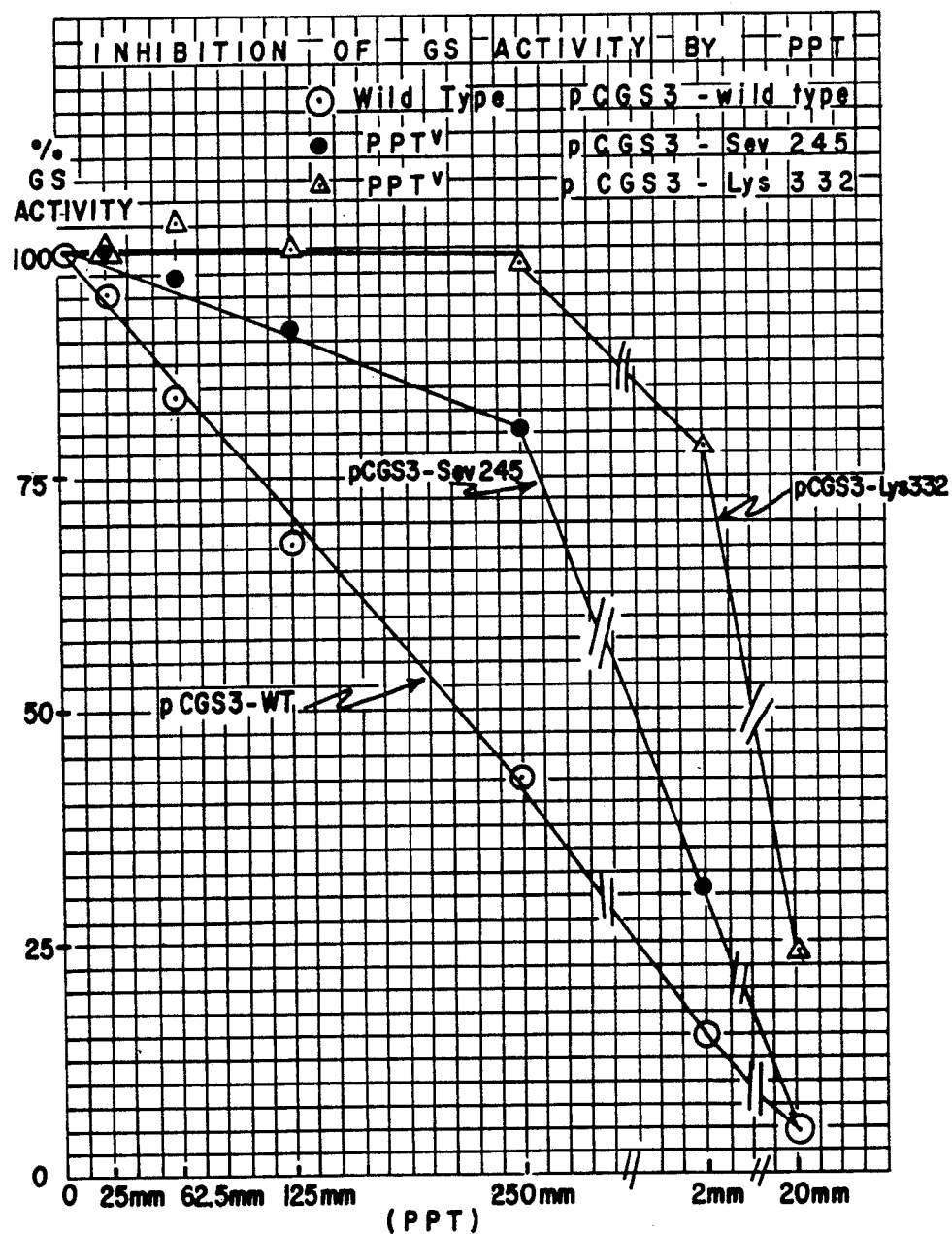

FIG. 7 is the graphical representation of the data in Table III showing the sensitivity of the wild type and PPT resistant GS enzymes to PPT.

FIG. 8 is the partial genetic sequence of the leaf-specific GS cDNA clone from Arabidopsis, AtcGSL1.

Figure 9A:
Figure 9B:
Figure 9C:

FIG. 9 is a Northern blot of Arabidopsis RNA isolated from leaves and roots and blotted with nick-translated probe of A. Arabidopsis leaf-specific cDNA clone AtcGSL1; B. Arabidopsis root-specific cDNA clone, AtcGSr1; C. Arabidopsis root-specific cDNA clone, AtcGSr2.

Figure 10:
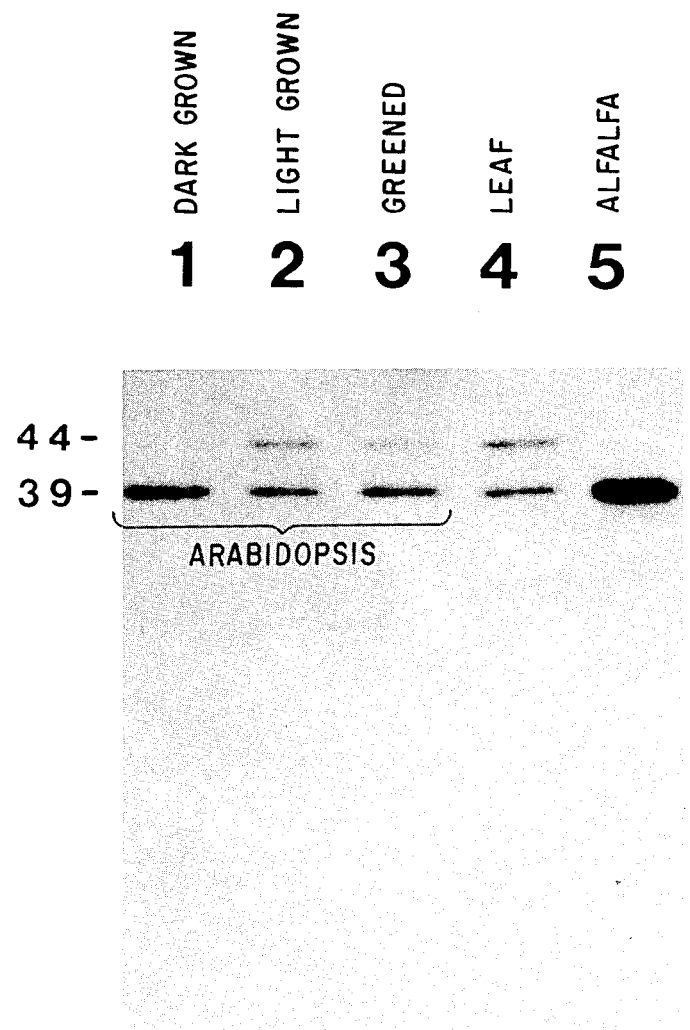

FIG. 10 is a Western blot (SDS-polyacrylamide gel probed with specific antisera against alfalfa GS and $^{125}$I-protein (A) using protein extracts from dark-grown, light-grown, and greened Arabidopsis seedlings, Arabidopsis leaves, and "Alfalfa," alfalfa tissue culture cells containing an amplified GS gene.

FIG. 11 is the partial genetic sequence of the root-specific GS cDNA clone from Arabidopsis. AtcGsr1.

FIG. 12 is the partial genetic sequence of the root-specific GS cDNA clone from Arabidopsis, AtcGSr2.

DESCRIPTION OF THE PREFERRED EMBODIMENTS

In one embodiment, the invention comprises a prokaryotic cell which, in its untransformed state, does not produce glutamine synthetase but, when transformed according to the invention, can produce wild type eukaryotic, or mutant eukaryotic or prokaryotic glutamine synthetase.

The definition of the enzyme "glutamine synthetase" is functional, and includes any glutamine synthetase capable of functioning in a given desired host, especially a bacterium or a plant, to convert glutamic acid to glutamine. The term therefore includes not only the enzyme from the specific plant species involved in the genetic transformation, but may include GS from other plant species or microbes, if such GS is capable of functioning in the transformed plant or bacterial cells. The term includes proteins or polypeptides having more or less than the total structural length of natural GS, such as functional partial fragments of GS, their analogues, or active variants. For example, GS lacking the normal second to fifth N-terminal amino acids (S, L, L, S), or having a glutamine residue instead of a histidine residue at position 249 are, in accordance with the studies shown herein, active enzymes, and which are, moreover, sensitive to PPT inhibition. Such enzymes are called "variants" herein.

The term "phosphinothricin" denotes the known compound, in its biologically active form. It may be the L-, or D,L- forms, and may be alone or in combination with other inert or active compounds which do not interfere with PPT activity.

The term "prokaryote" is meant to include bacteria, bacteriophages and viruses, whereas, the term "eukaryote" includes plants, animals, fungi, yeasts, and parasites.

WILD TYPE GS

The wild type glutamine synthetase may be from any eukaryotic source. All that is necessary is that the genetic sequence for the enzyme be expressed, and produce, a functional enzyme in a prokaryotic cell. Preferred are plant glutamine synthetase genes and their expression products. Of particular interest are glutamine synthetase genes from particular plant species which are of agricultural importance, especially herbicidal GS inhibitor sensitive plants.

The wild type gene for glutamine synthetase from any plant cell as described which is capable of undergoing genetic manipulation by genetic constructs can be used to transform a prokaryotic cell not expressing glutamine synthetase. Among dicotyledonous plants which can be used as source for the wild type glutamine synthetase gene are included various species of potato (*Solanum tuberosum*); tomato (*Lycopersicon esculentum*); pepper (*Capsicum annumm*); tobacco (*Nicotiana tabacum*); various species of Brassica, especially rapeseed (*Brassica napus*), various legumes, for example alfalfa (*Medicago sativa*), clover (*Trifolium sp*), soybean (*Glycine max*), groundnut (*Arachis hypogaea*); various species of beans (*Phaseolus sp., Vici sp., Vigna sp.*); peas (*Pisum Sativum*); root crops such as beets (*Beta vulgaris*), carrots (*Daucus carota*), and sweet potatoes (*Ipomoea batatus*); and others, such as *Arabidopsis thaliana*.

The wild type gene can be obtained from any plant organ, such as roots, leaves, stems, and the like. In *A. thaliana* the genes for wild type GS are leaf-specific and root specific. The leaf-specific gene is of interest as it is light inducible, and codes for a 44 Kd polypeptide. (See Example 5-8.) The organ specificity of these genes is of interest, as they allow organ specific transformation and/or expression of mutant GS genes which are PPT resistant (see below).

The eukaryotic gene for wild type glutamine synthetase can be derived directly from the eukaryotic DNA of cells of plants or via cDNA derived from the eukaryotic mRNA. Techniques for the isolation of eukaryotic glutamine synthetase are described in copending U.S. Pat. application Ser. No.833,156, filed Feb. 27, 1986 which is herein incorporated by reference.

A recombinant DNA molecule comprising a sequence coding for the wild type eukaryotic glutamine synthetase can be used to transform a prokaryote using any of the techniques commonly known to those of ordinary skill in the art. Especially preferred is the use of a plasmid containing cDNA for the eukaryotic wild type glutamine synthetase coding sequence, for prokaryotic transformation.

Methods for preparing fused, operably linked genes and expressing them in bacteria are known and are shown, for example, in U.S. Pat. No. 4,366,246. The genetic constructs and methods described therein can be utilized for expression of glutamine synthetase in prokaryotic hosts.

Prokaryotic hosts may include Gram negative and Gram positive bacteria, such as *E. coli., S. typhimurium, Serratia marsescens*, and *Bacillus subtilis*. The preferred bacterial host for expression is a mutant strain which, unlike the wild strain from which the mutant is derived, is no longer able to express its own functional prokaryotic glutamine synthetase or which produces lower levels of glutamine synthetase activity. These mutant strains have lost the ability to produce functional glutamine synthetase, or produce lower levels of glutamine synthetase than the wild-type or parent strain, or produce a glutamine synthetase with diminished activity, due to a mutation. Most preferred are mutant strains of *E. coli* which have lost the ability to produce their own functional glutamine synthetase.

In general, expression vectors containing promoter sequences which facilitate the efficient transcription of the inserted gene fragment, which are derived from species compatible with the host cells, are used in connection with the prokaryotic host. The expression vector typically contains an origin of replication, promoter(s), terminator(s), as well as specific genes which are capable of providing phenotypic selection in transformed cells. The transformed host can be fermented and cultured according to means known in the art to achieve optimal cell growth.

Examples of prokaryotic promoters which can be used in the invention are rec A, trp, lac, tac, and bacteriophage lambda $p_R$ or $p_L$. Examples of plasmids which can be used in the invention are listed in Maniatis et al., *Molecular Cloning*, Cold Spring Harbor Laboratory, 1982.

In one aspect of the present invention, the complete alfafa GS coding sequence devoid of introns was reconstructed by joining the 5'-terminal 70 bp GS coding sequence present in a clone of a GS nuclear gene to the 3'-terminal 1000 bp GS coding sequence present in the cDNA. The resulting construct, pGS100, was cleaved with BglII and StuI to produce a 1.2 kbp DNA fragment containing an uninterrupted and nearly complete GS coding region missing only 14 nucleotides at the 5'-end. The 1.2 kbp BglII/StuI fragment was cloned into the *E. coli* expression vector ptac1212 which regenerated the entire GS coding sequence and placed it downstream from the bacterial tac promoter and lacZ ribosome binding site. This resulted in the GS expression plasmid pCGS2.

The invention extends to any bacterium modified according to the methods described, or modified by any other methods, common to those of ordinary skill such as, for example, by transfer of genetic material using a lysogenic phage, and which yield a prokaryote expressing a wild type eukaryotic glutamine synthetase.

More specifically, in one embodiment of the present invention, the expression in *E. coli* of the alfalfa wild type GS gene as constructed in pCGS2 was initially demonstrated by genetic complementation in GS deficient (glnA) bacterial mutant FDB213.

MUTANT GS

The prokaryotes transformed with eukaryotic glutamine synthetase as above are particularly useful for the production of structural mutants coding for glutamine synthetase which retains metabolic activity, but is resistant to inhibitors of glutamine synthetase, especially herbicidal GS inhibitors, such as PPT. In addition, commercial production of glutamine synthetase can also be carried out.

The term "herbicidal glutamine synthetase inhibitor" is meant to include any inhibitor, competitive or noncompetitive, that significantly decreases the glutamine synthetase activity of a plant cell of a given species and, as a consequence thereof, causes herbicidal effects in the plant cell. Examples of GS inhibitors are phosphinothricin, methionine sulfoximine, as well as other glutamic acid analogues.

Spontaneous mutation is a common occurrence in microorganisms, and mutations can be intentionally produced by a variety of known procedures. For example, mutants can be induced using chemical, radiation, and recombinant DNA techniques.

Examples of chemical mutagens are base analogues, deaminating agents, alkylating agents, and acridine derivatives.

Radiation-induced mutations can be caused by such agents as ultraviolet light, and X-rays. The primary mechanism by which these mutations may be caused results from excision or post-replication repair by recombination.

Additionally, mutations can also be produced by recombinant DNA techniques known as "site directed mutagenesis" using restriction endonucleases or syntheses primed by mutant oligonucleotides. Use of these techniques is especially valuable to allow the deletion or insertion of large DNA fragments, or point mutants at specific locations.

Regardless of the manner in which the mutations are induced, the important issue is that the resulting mutants produce functional glutamine synthetase which is resistant to (that is, less inhibited by) herbicidal GS inhibitors.

Thus, in another embodiment, the present invention relates to GS mutants wherein the glutamine synthetase which is produced is less sensitive to the action of such herbicides as, for example, phosphinothricin, as compared to the wild type glutamine synthetase.

This embodiment also extends to the mutant GS polypeptides, substantially in purified form or in foreign host cells.

The mutant GS genes can be obtained by mutation of a wild-type GS from any source. Of particular interest are the mutants derived from leaf and/or root-specific GS, especially those derived from light inducible, leaf-specific GS genes.

This embodiment of the invention therefore provides for genetic sequences coding for mutant GS enzymes, preferably GS enzymes resistant to inhibition by PPT.

Specific mutations which result in PPT resistance are a change of amino acid residue gly 245 (as numbered in FIG. 6, i.e. including a starting methionine residue which may or may not otherwise be present depending on whether expression occurs in bacteria) to residue ser 245, hereinafter "GS (ser 245)." This is accomplished by modifying the corresponding codon from GGT (for gly 245) to AGT (for ser 245). GS (ser 245) is a functionally active enzyme which, however, is not inhibited by normally inhibitory concentrations of PPT.

Other PPT resistant mutants also result from changes in amino acid residue gly 245, for example, to arg 245 ("GS (arg 245)"), and to cys 245 ("GS (cys 245)").

Thus, it is concluded that replacement of ser 245 by another amino acid X will result in a PPT resistant GS mutant. A PPT resistant mutant of GS having any amino acid replacement X at position 245 will be denoted as "GS (X 245)."

The new amino acid at position 245 can be neutral, acid, or basic, preferably neutral or basic. Neutral amino acids include ala, cys, ile, leu, met, phe, pro, gln, asn, ser, thr, tyr, and val. Basic ones include arg, his, trp, and lys.

Yet another PPT resistant mutant is obtained by replacing arginine at position 332 by lysine, to yield GS (lys 332).

As indicated above, GS lacking the normally N-terminal amino acid residues #2–5 (SLLS), or with gln at position 249 instead of his at that position ("GS (gln 249)") are active variants, and PPT sensitive. GS (val 207) is a partially active variant. Therefore, GS(X245), such as GS (ser 245), GS (arg 245), GS cys 245), or GS (lys 332), having the further mutations gln 249 and/or lacking the normally N-terminal amino acids S, L, L, S are also included among the PPT resistant mutant enzymes of this invention.

In particular the invention relates to a mutant glutamine synthetase enzyme having the following amino acid sequence:

| 1 | M | S | L | L | S | D | L | I | N | L | D | L | S | E | T | T | E | K | I | I |
|---|---|---|---|---|---|---|---|---|---|---|---|---|---|---|---|---|---|---|---|---|
| 21 | A | E | Y | I | W | I | G | G | S | G | L | D | L | R | S | K | A | R | T | L |
| 41 | P | G | P | V | T | D | P | S | Q | L | P | K | W | N | Y | D | G | S | S | T |
| 61 | G | Q | A | P | G | E | D | S | E | V | I | I | Y | P | Q | A | I | F | K | D |
| 81 | P | F | R | R | G | N | N | I | L | V | M | C | D | A | Y | T | P | A | G | E |
| 101 | P | I | P | T | N | K | R | H | A | A | A | K | I | F | S | H | P | D | V | V |
| 121 | A | E | V | P | W | Y | G | I | E | Q | E | Y | T | L | L | Q | K | D | I | N |
| 141 | W | P | L | G | W | P | V | G | G | F | P | G | P | Q | G | P | Y | Y | C | G |
| 161 | A | G | A | D | K | A | F | G | R | D | I | V | D | S | H | Y | K | A | C | L |
| 181 | Y | A | G | I | N | I | S | G | I | N | G | E | V | M | P | G | Q | W | E | F |
| 201 | Q | V | G | P | S | V | $X^1$ | I | S | A | G | D | E | I | W | V | A | R | Y | I |
| 221 | L | E | R | I | T | E | V | A | G | V | V | L | S | F | D | P | K | P | I | K |
| 241 | G | D | W | N | $X^2$ | A | G | A | H | T | N | Y | S | T | K | S | M | R | E | D |
| 261 | G | G | Y | E | V | I | L | K | A | I | E | K | L | G | K | K | H | K | E | H |
| 281 | I | A | A | Y | G | E | G | N | E | R | R | L | T | G | R | H | E | T | A | D |
| 301 | I | N | T | F | L | W | G | V | A | N | R | G | A | S | I | R | V | G | R | D |
| 321 | T | E | K | A | G | K | G | Y | F | E | D | $X^3$ | R | P | S | S | N | M | D | P |
| 341 | Y | V | V | T | S | M | I | A | D | T | T | I | L | W | K | P | | | | | where $X^1$ at 207 is G;
$X^2$ at 245 represents an amino acid different than glycine; and
$X^3$ at 332 is arginine or lysine.

With this knowledge in hand, it is possible to construct genes and rDNA molecules containing the genes by synthesis, recombination or splicing, and the mutant GS genetic sequences need therefore no longer be of strictly "eukaryotic" or "prokaryotic" origin.

Prokaryotic hosts comprising mutant GS genetic sequences, and capable of expressing the same are then prepared by the same methods, and using the same materials as those described above for the wild type eukaryotic enzyme.

RESISTANT PLANT CELLS

In a third embodiment, the invention is directed to recombinant DNA molecules containing the mutant GS gene. These rDNA molecules confer herbicidal tolerance to plant cells and plants by rendering the cells resistant to a herbicidal GS inhibitor. Specifically then, this invention further relates to rDNA molecules comprising a genetic sequence coding for a mutant GS polypeptide and to herbicidal tolerant, transformed plant cells, and to plants expressing such mutant GS.

The term "herbicidal tolerant plant" as used herein is defined as a plant that survives and grows at least effectively and preferably normally at the usually effective dose of a herbicidal GS inhibitor. Resistance is the maximum tolerance that can be achieved. Thus, the term "herbicidal tolerance" as used herein is meant to include herbicidal tolerant plants and herbicidal resistant plants. The herbicidal tolerant plant will survive without damage in the presence of herbicidal GS inhibitors that are lethal to or that damage the growth or vigor of herbicidal sensitive plants.

Any plant cell and plant capable of expressing the mutant GS gene may be transformed by this invention. These plants should also be capable of undergoing genetic manipulation by genetic engineering techniques. As used herein, the term "plant" includes plant cells, plant protoplasts, plant tissue culture that can be cultured and induced to form plants, plant calli, plant clumps and plant cells that are intact in plants or parts of plants. "Plant" also refers to pollen that may be transformed by genetic engineering techniques.

The coding region for the mutant GS that may be used in this invention may be homologous or heterologous to the plant cell or plant being transformed. It is necessary, however, that the genetic sequence coding for GS be expressed, and produced, as a functional enzyme or polypeptide in the resulting plant cell. Thus, the invention comprises plants containing either homologous GS genes or heterologous GS genes that express the mutant GS enzyme. Further, the GS may be from other plant species, or from different organisms, such as microbes or mammals.

Since the mutant GS is present in the plant cell the glutamine/glutamate metabolism can continue normally, even in the presence of GS inhibitors.

DNA from both genomic DNA and cDNA encoding for the mutant GS gene may be used in this invention. Further, the GS gene may be constructed partially of a cDNA clone and partially of a genomic clone. In addition, the DNA coding for the mutant GS gene may comprise portions from various plant, microbial, and animal GS enzymes.

There are a variety of aspects encompassed in this embodiment of the invention. In one of its aspects, this embodiment comprises chimeric genetic sequences with:

(a) a first genetic sequence coding for a mutant GS polypeptide that upon expression of the gene in a given plant cell is functional for GS activity; and
(b) one or more additional genetic sequences operably linked on either side of the GS coding region. These additional genetic sequences contain sequences for plant cell promoter(s) or terminator(s). The plant regulatory sequences may be heterologous or homologous to the host cell.

Promoters that may be used in the chimeric genetic sequence include nos, ocs, and CaMV promoters.

The chimeric genetic sequence comprising the mutant GS gene operably linked to a promoter capable of operating in a plant cell can be ligated into a suitable cloning vector. In general, plasmid or viral vectors containing replication and control sequences derived from species compatible with the plant host cell are used. The cloning vector will typically carry a replication origin, as well as specific genes that are capable of providing phenotypic selection markers in transformed host cells, typically resistance to antibiotics or resistance to selected herbicides. The transforming vectors can be selected by these phenotypic markers after transformation in a host cell.

The cloning vector and host cell transformed with the vector are used in this invention typically to increase the copy number of the vector. With an increased copy number, the vectors containing the GS gene can be isolated and, for example, used to introduce the chimeric genetic sequences into the plant cells.

The genetic material contained in the vector can be microinjected directly into plant cells by use of micropipettes to mechanically transfer the recombinant DNA. The genetic material may also be transferred into the plant cell by using polyethylene glycol. This forms a precipitation complex with the genetic material that is taken up by the cell. (Paszkowski et al., *EMBO J.*, 3: 2717-22 (1984)).

In an alternate embodiment of this invention, the GS gene may be introduced into the plant cells by electroporation. (Fromm et al., "Expression of Genes Transferred into Monocot and Dicot Plant Cells by Electroporation," *Proc. Nat'l Acad. Sci. U.S.A.*, 82: 5824 (1985)). In this technique, plant protoplasts are electroporated in the presence of plasmids containing the GS genetic construct. Electrical impulses of high field strength reversibly permeabilize biomembranes allowing the introduction of the plasmids. Electroporated plant protoplasts reform the cell wall, divide, and form plant callus. Selection of the transformed plant cells with the expressed GS enzyme can be accomplished using the phenotypic markers as described above.

Cauliflower mosaic virus (CaMV) may also be used as a vector for introducing the GS gene into plant cells in this invention. (Hohn et al., in "Molecular Biology of Plant Tumors," Academic Press, New York, 1982 Pages 549-560; Howell, U.S. Pat. No. 4,407,956)). The entire CaMV viral DNA genome is inserted into a parent bacterial plasmid creating a recombinant DNA molecule which can be propagated in bacteria. After cloning, the recombinant plasmid is cleaved with restriction enzymes either at random or at unique sites in the viral portion of the recombinant plasmid for insertion of the GS genetic sequence. A small oligonucleotide, described as a linker, having a unique restriction site may also be inserted. The modified recombinant plasmid again may be cloned and further modified by introduction of the GS genetic sequence thereof into the unique restriction site of the linker. The modified viral portion of the recombinant plasmid is then excised from the parent bacterial plasmid, and used to inoculate the plant cells or plants.

Another method of introducing the GS gene into plant cells is to infect a plant cell with *Agrobacterium tumefaciens* transformed with the GS gene. Under appropriate conditions known in the art, the transformed plant cells are grown to form shoots, roots, and develop further into plants. The GS genetic sequences can be introduced into appropriate plant cells, for example, by means of the Ti plasmid of *Agrobacterium tumefaciens*. The Ti plasmid is transmitted to plant cells on infection by *Agrobacterium tumefaciens*, and is stably integrated into the plant genome. Horsch et al., "Inheritance of Functional Foreign Genes in Plants," *Science*, 233:

496–498 (1984); Fraley et al, *Proc. Nat'l Acad. Sci. U.S.A.*, 80: 4803 (1983).

Ti plasmids contain two regions essential for the production of transformed cells. One of these, named transfer DNA (T DNA), induces tumor formation. The other, termed virulent region, is essential for the formation but not maintenance of tumors. The transfer DNA region, which transfers to the plant genome, can be increased in size by the insertion of the GS genetic sequence without its transferring ability being affected. By removing the tumor-causing genes so that they no longer interfere, the modified Ti plasmid can then be used as a vector for the transfer of the gene constructs of the invention into an appropriate plant cell.

All plant cells which can be transformed by *Agrobacterium* and whole plants regenerated from the transformed cells can also be transformed according to the invention so to produce transformed whole plants which contain the transferred GS gene.

There are presently two different ways to transform plant cells with *Agrobacterium*:

(1) co-cultivation of *Agrobacterium* with cultured isolated protoplasts, or
(2) transformation of cells or tissues with *Agrobacterium*.

Method (1) requires an established culture system that allows culturing protoplasts and plant regeneration from cultured protoplasts.

Method (2) requires (a) that the plant cells or tissues can be transformed by *Agrobacterium* and (b) that the transformed cells or tissues can be induced to regenerate into whole plants. In the binary system, to have infection, two plasmids are needed: a T-DNA containing plasmid and a vir plasmid. Any one of a number of T-DNA containing plasmids can be used. The only requirement is that one be able to select independently for each of the two plasmids.

After transformation of the plant cell or plant, those plant cells or plants transformed by the Ti plasmid so that the GS enzyme is expressed, can be selected by an appropriate phenotypic marker. These phenotypic markers include, but are not limited to, antibiotic resistance or herbicide resistance. Other phenotypic markers are known in the art and may be used in this invention.

All plants from which protoplasts can be isolated and cultured to give whole regenerated plants can be transformed by the present invention so that whole plants are recovered which contain the transferred GS gene. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Ciohorium, Helianthus, Lactuca, Bromus, Asparagus, Antirrhinum, Hemerocallis, Nemesia, Pelargonium, Panicum, Pennisetum, Ranunoulus, Senecio, Salpiglossis, Cucumis, Browallia, Glycine, Lolium, Zea, Triticum, Sorghum, and Datura.

It is known that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. Hooykas-Van Slogteren et al, *Nature*, 311:763-764 (1984). There is growing evidence now that certain monocots can be transformed by Agrobacterium. Using novel experimental approaches that have now become available, cereal and grass species may be transformed.

Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus and Pisum.

Plant regeneration from cultural protoplasts is described in Evans, et al., "Protoplast Isolation and Culture," in *Handbook of Plant Cell Culture*, 1:124-176 (MacMillan Publishing Co. New York 1983); M.R. Davey; "Recent Developments in the Culture and Regeneration of Plant Protoplasts," *Protoplasts*, 1983—Lecture Proceedings, pp. 19-29, (Birkhauser, Basel 1983); P.J. Dale, "Protoplast Culture and Plant Regeneration of Cereals and Other Recalcitrant Crops," in *Protoplasts* 1983—Lecture Proceedings, pp. 31-41, (Birkhauser, Basel 1983); and H. Binding, "Regeneration of Plants," in *Plant Protoplasts*, pp. 21-37, (CRC Press, Boca Raton 1985).

Regeneration varies from species to species of plants, but generally a suspension of transformed protoplasts containing copies of the GS gene is first provided. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the gene for the mutant GS enzymatic activity level. These seeds can be grown to produce plants that are herbicidal GS inhibitor tolerant. The tolerance of these seeds can be determined, for example, by growing the seeds in soil containing a herbicide. Alternatively, the herbicidal tolerance of the transformed plants can be determined by applying herbicide to the plant.

The inbreds according to this invention can be used to develop herbicidal tolerant hybrids. In this method a herbicidal tolerant inbred line is crossed with another herbicidal tolerant inbred line to produce the hybrid.

Parts obtained from the regenerated plant, such as flowers, seeds, leaves, branches, fruit, and the like are covered by the invention, provided that these parts comprise the herbicidal tolerant cells. Progeny and variants, and mutants of the regenerated plants are also included within the scope of this invention.

Uses for GS Genetic Constructs and Herbicidal Resistant Plants

The GS genetic constructs, as previously described, may be used in vectors as intermediates in the preparation of herbicidal resistant plant cells, plant organs, plant tissues, and plants.

The importance of a herbicidal tolerant plant according to the invention is obvious. The herbicidal resistant plant enables the farmer to plant a herbicidal tolerant crop and then treat the field for weeds without adversely affecting the crop. Further, the herbicidal tolerant plant enables the farmer to grow crops in fields that have been treated with herbicides. These herbicidally treated fields will contain a certain amount of the herbicide in the soil and thus a "herbicide carryover" is seen.

The invention thus also encompasses a method of plant control which comprises contacting a herbicide sensitive plant, such as a weed, with plant controlling amounts of a herbicidal GS inhibitor, wherein the contact is carried out while the sensitive plant is present simultaneously with the herbicide tolerant plants of the invention. Thus, foliar herbicidal treatment of plants in a field or cultivar, with both herbicidal tolerant plants and herbicidal sensitive plants, and wherein both plant types are simultaneously contacted with the herbicide during the treatment operation, is a method included in the present invention.

By the term "plant controlling amounts of herbicide" is meant to include functionally, an amount of herbicide which is capable of affecting the growth or development of a given plant. Thus, the amount may be small enough to simply retard or suppress the growth or development, or the amount may be large enough to irreversibly destroy the sensitive plant. Normally, most dicotyledonous plants and weeds may be controlled at rates of between 0.5 to 1.5 kg/ha ai. For monocotyledonous plants, rates between 0.5 kg/ha ai, and up to about 2.0 kg/ha ai are normally used. The herbicide can, of course, be contacted with the appropriate plant using well known spraying or spreading methods.

Having now generally described the invention, a more complete understanding can be obtained by reference to the following specific examples. These examples are provided for purposes of illustration only, and are not intended to be limiting unless otherwise specified.

EXAMPLE 1

Figure 1:
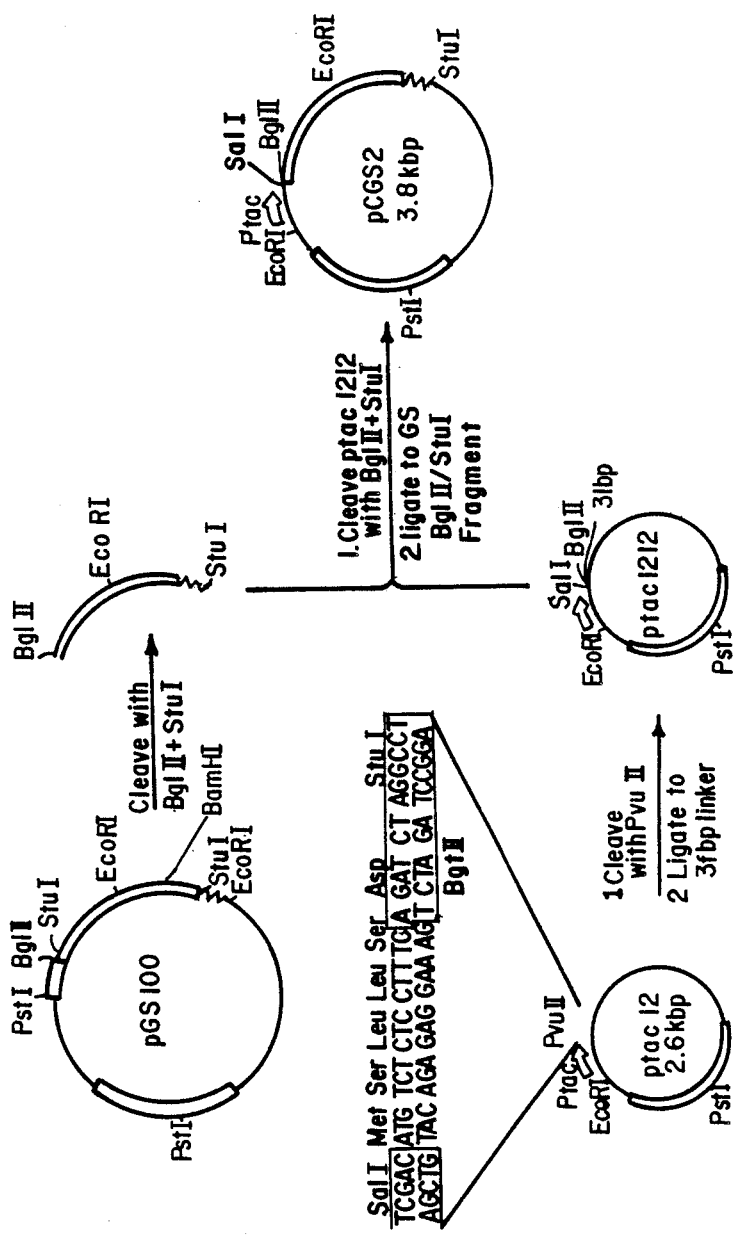
FIG. 1 illustrates the construction of the alfalfa wild type glutamine synthetase expression plasmid, pCGS2, and intermediate plasmids pGS100 and ptac1212.

Construction of an Alfalfa Glutamine Synthetase Expression Plasmid and Intermediate Plasmids The construction of a complete alfalfa cDNA in pGS100 was accomplished by cloning two cDNA restriction fragments and a genomic DNA restriction fragment into pSP65 in two steps (Melton et al., *Nucleic Acid Research*, 12: 7035, 1984). First, a 270 bp BamHI/EcoRI, cDNA fragment encoding the 3'-end of the GS coding region and the 3'-noncoding region was cloned into pSP65 at the polylinker BamHI and EcoRI sites. Second, this construct was cleaved with BamHI and AccI in the polylinker site and ligated simultaneously with a 950 bp NdeI/BamHI internal cDNA fragment and a 310 bp AccI/NdeI genomic DNA fragment encoding the 5'-end of the GS coding region to form pGS100. For construction of ptac1212, a 31 bp synthetic oligonucleotide was cloned into the PvuII site of ptac12 (Amann et al., *Gene*, 25: 167, 1983). The sequence of the oligonucleotide is indicated above ptac12 in FIG. 1. For construction of pCGS2, the 1.2 kbp BglII/StuI fragment isolated from pGS100 was cloned into the BglII and StuI sites of ptac1212. The accuracy of the final construction was confirmed by restriction mapping using EcoRI, SalI, BglII, NdeI, BamHI, and StuI, and DNA sequence analysis across the tac promoter and the 5'-terminal coding region of GS by the chain termination method (Sanger et al., *Proceedings of the National Academy of Sciences, USA*, 74: 5463, 1977). Standard procedures were followed for all constructions (Amman et al., *Gene* 25: 167, 1983; Maniatis et al., *Molecular Cloning*, Cold Spring Harbor Laboratory, 1982). All vectors containing promoters were propagated in *E. coli* W3110laci$^q$ (Amman et al., *Gene* 25: 167, 1983).

EXAMPLE 2

Expression in *E. Coli* of Wild Type Alfalfa Glutamine Synthetase Gene

The expression in *E. coli* of the engineered wild type alfalfa glutamine synthetase gene was initially demonstrated by genetic complementation of a glutamine synthetase deficient ( glnA) bacterial mutant (deBrujin et al., *Molecular and General Genetics*, 183: 289, 1981). *E. coli* FDB213, which has a deletion in the endogeneous GS gene, was transformed with the alfalfa GS expression plasmid, pCGS2, prepared in Example 1. The parental and pCGS2 containing strains were streaked out on M9 minimal media (supplemented with thiamine-HCl and proline) containing or lacking glutamine. As shown in FIG. 2, the FDB213 parental strain can grow only on medium containing glutamine (Section A), but the FDB213(pCGS2) derivative is prototrophic and can grow on media containing or lacking glutamine (Section B). Thus, alfalfa GS must be synthesized in *E. coli* and, furthermore, must at least partially fold and assemble into a catalytically active enzyme. Consistent with this conclusion, GS enzyme activity was detected in FDB213(pCGS2) but not in FDB213(ptac 1212) or FDB213 using the hemibiosynthetic enzyme assay (McCormack et al., *Archives of Biochemistry and Biophysics*, 218:561, 1982).

In FIG. 2, the complementation of FDB213 by the alfalfa GS gene in pCGS2 was tested at a high ammonium chloride concentration (18 mM), requiring that alfalfa GS catalyze the synthesis of glutamine necessary for protein synthesis, but not necessarily function as part of the primary pathway for assimilation of ammonia. Bacterial glutamate dehydrogenase can carry out the assimilation of ammonia at high ammonium concentrations. However, in medium containing low ammonium concentration ($\leq$0.5 mM) or an alternate nitrogen source (for example, L-arginine), assimilation of ammonia requires the GS/glutamate synthase cycle. This is due to the relatively higher $K_m$ for ammonia and lower reaction equilibrium constant in the case of glutamate dehydrogenase compared to GS (Mora, et al., Eds., *Glutamine: Metabolism, Enzymology, and Regulation*, Acad. Press, New York, 1980; Magasanik, *Annual Reviews of Genetics*, 16:135, 1982). Thus, to determine if alfalfa GS can function in the assimilation of ammonia in *E. coli*, the ability of FDB213 (pCGS2) to grow in minimum media containing either a low concentration of ammonium chloride (0.5 mM and 0.1 mM) or L-arginine (0.2%) as the soul nitrogen source was tested. The FDB213 (pCGS2) strain could grow at 0.5 mM ammonium chloride concentration (the generation time being four times longer than at 5 mM), but could not grow at 0.1 mM ammonium chloride concentration or using L-arginine as the sole nitrogen source. These results suggest that assimilation of ammonia cannot be carried out efficiently in alfalfa GS in *E. coli*, assuming that the $K_m$ for ammonia for the plant enzyme is similar to that for the bacterial enzyme.

The synthesis of alfalfa GS enzyme in *E. coli* was confirmed by immunoblotting analysis (Burnett, *Analytical Chemistry*, 112: 195, 1981). *E. coli* W3110 *lacI*q containing pCGS2 was grown in the presence or absence of inducer (isopropylthio-beta-D-galactoside (IPTG)). The cells were harvested by centrifugation, lysed, and fractionated on denaturing and nondenaturing gels.

Figures 3A, 3B:
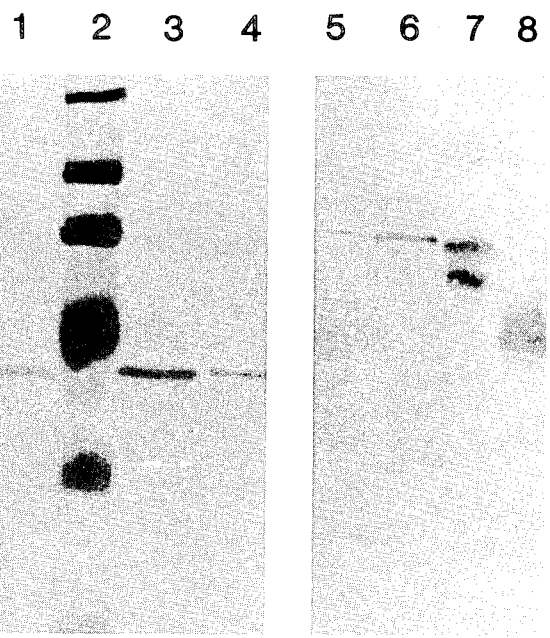
FIG. 3 shows the immunoblot analysis of alfalfa wild type glutamine synthetase expressed in *E. coli* under denaturing (A) and non-denaturing (B) conditions.

Cells from which protein extracts were to be fractionated on denaturing gels were lysed by addition of a solution containing 125 mM Tris-HCl (pH 7), 0.5% SDS, 10% glycerol, 0.7M 2-mercaptoethanol and heating at 100 degrees C for 5 minutes. Total cell protein was fractionated on a 10% polyacrylamide-SDS gel (Laemmli, *Nature* (London) 227:680, 1970) alongside prestained molecular weight markers (Bethesda Research Laboratories) and partially purified alfalfa GS (Donn et al., *Journal of Molecular and Applied Genetics*, 2:621, 1984). The proteins were transferred to nitrocellulose by electroblotting, incubated first with alfalfa GS antiserum, followed by staphylococcal Protein A-horseradish peroxidase conjugate and developed by colorimetric assay (Burnette, *Analytical Biochemistry*, 112: 195, 1981; Avrameras et al., *European Journal of Immunolology*, 1: 394, 1971). Antiserum to purified alfalfa glutamine synthetase was prepared by injecting rabbits (Donn et al., *Journal of Molecular and Applied Genetics*, 2:621, 1984). The results of this study are shown in FIG. 3(A). Lane 1 contains material from *E. coli* (pCGS2) which was uninduced; Lane 2 prestained protein molecular weight markers (myosin H-chain, 200,000; phosphorylase B, 97,400; bovine serum albumin, 68,000; ovalbumin, 43,000; alpha-chymotrypsinogen, 25,700; betalactoglobulin, 18,400); Lane 3 contains protein from *E. coli* (pCGS2) induced with IPTG; and Lane 4 contains purified alfalfa GS enzyme. A single band is visible for the *E. coli* extracts (lanes 1 and 3) which comigrates with authentic alfalfa GS (lane 4).

Cells from which protein extracts were to be fractionated on non-denaturing gels were grown and collected as described above, but were also treated with 10 mg/ml lysozyme at high cell density. The cells were lysed by sonication, clarified by centrifugation, and the cell lysates fractionated on a native 5% polyacrylamide gel (Davis, *Annals of the New York Academy of Sciences*, 121: 404, 1964) alongside crude extract from the 3mM L-phosphinothricin resistant alfalfa suspension cell line (Donn et al., *Journal of Molecular and Applied Genetics*, 2:621, 1984). Immunoblotting analysis (FIG. 3(B)) was performed as described above. Lane 5 contains *E. coli* (pCGS2) uninduced; Lane 6 contains *E. coli* (pCGS2) induced with IPTG; Lane 7 contains crude extract from alfalfa; and Lane 8 contains denatured alfalfa GS. A single band is visible for the *E. coli* extracts (lanes 5 and 6) which comigrates with the upper band in the plant extract (lane 7).

The results of these experiments show that pCGS2 directs the synthesis in *E. coli* of a protein which cross-reacts with alfalfa GS antiserum and comigrates with alfalfa GS on both denaturing and non-denaturing, gels (see, Lanes 3 and 4, and Lanes 6 and 7, respectively). When the untransformed parental strain of *E. coli* was analyzed in a similar manner these bands were not present (data not shown).

The results of these experiments also confirm that the expected subunit molecular weight and native structure of the protein detected in *E. coli* (pCGS2) was that of plant GS. The subunit molecular weight of alfalfa GS based on polyacrylamide-SDS gel analysis (39,000) is consistent with the molecular weight predicted from the DNA sequence of the GS gene. *E. coli* GS has a subunit molecular weight of 55,000 (Mora et al., *Glutamine: Metabolism Enzymology, and Regulation*, Academic Press, 1980) and does not visibly cross-react in these experiments with antiserum to plant GS. The relatively slow migration of GS on the native gel is consistent with the known octameric quarternary structure of eukaryotic GS enzymes (Mora et al., ibid). As indicated by the distribution of protein in the gels, essentially all of the soluble plant GS enzyme in *E. coli* appears to be in the native conformation, indicating that it is efficiently folded and assembled. An additional conclusion from this work is that a single alfalfa GS polypeptide species is sufficient to form a catalytically active enzyme (Lara et al., *Plant Physiology*, 76:1019, 1984).

The results described above indicate that the tac promoter is capable of directing the efficient synthesis of alfalfa GS in *E. coli*. As shown in FIG. 3, GS protein is synthesized in detectable amounts even under repressed conditions. Similarly, complementation of an *E. coli* glnA mutant requires only repressed levels of alfalfa GS (FIG. 2). The induction with IPTG resulted in a 3-5 fold higher level of GS synthesis (see, FIG. 3, Lanes 1 and 3, Lanes 5 and 6) to constitute about 1% of the total cell protein. In other studies, it has been shown that fusion of the tac promoter to the *E. coli* malPQ operon also resulted in qualitatively similar results (Vidal-Ingigliardi et al., *Nucleic Acid Research*, 5919, 1985). This presumably reflects properties of the tac promoter.

*E. coli* strain W3110 lac iq(pCGS2), containing alfalfa GS in plasmid pCGS2, was deposited on March 13, 1986, at the American Type Culture Collection (ATCC), Rockville, Maryland, and given accession number 67031. This *E. coli* strain was selected as the deposit host for the plasmid pCGS2 due to the greater long-term stability of the plasmid in this organism.

EXAMPLE 3

Preparation of a PPT Resistant GS Mutant, GS (Ser 245)

A. Introduction

The initial mutagenicity experiments were carried out with *E. coli* FDB213 (pCGS2), by growing overnight in M9/pro/thi to stationary phase and plating an aliquot in 10mM D,L-PPT. Resistant colonies were observed; they were picked and tested for resistance to PPT and MSO, and all showed resistance to both compounds whereas parental strains did not. The mutants were grown overnight, three were isolated, and glutamine synthetase enzyme activity was assayed in the presence or absence of PPT. The results, however, indicated that the mode of resistance appeared to be 7 to 10 fold overproduction of GS in the three mutants. Therefore, these initial experiments did not yield a structural mutant. Further experiments, carried out with a modified plasmid containing a beta-gal gene linked to the GS gene were then carried out, as follows.

B. Construction of Plasmid pCGS3

Figure 4:
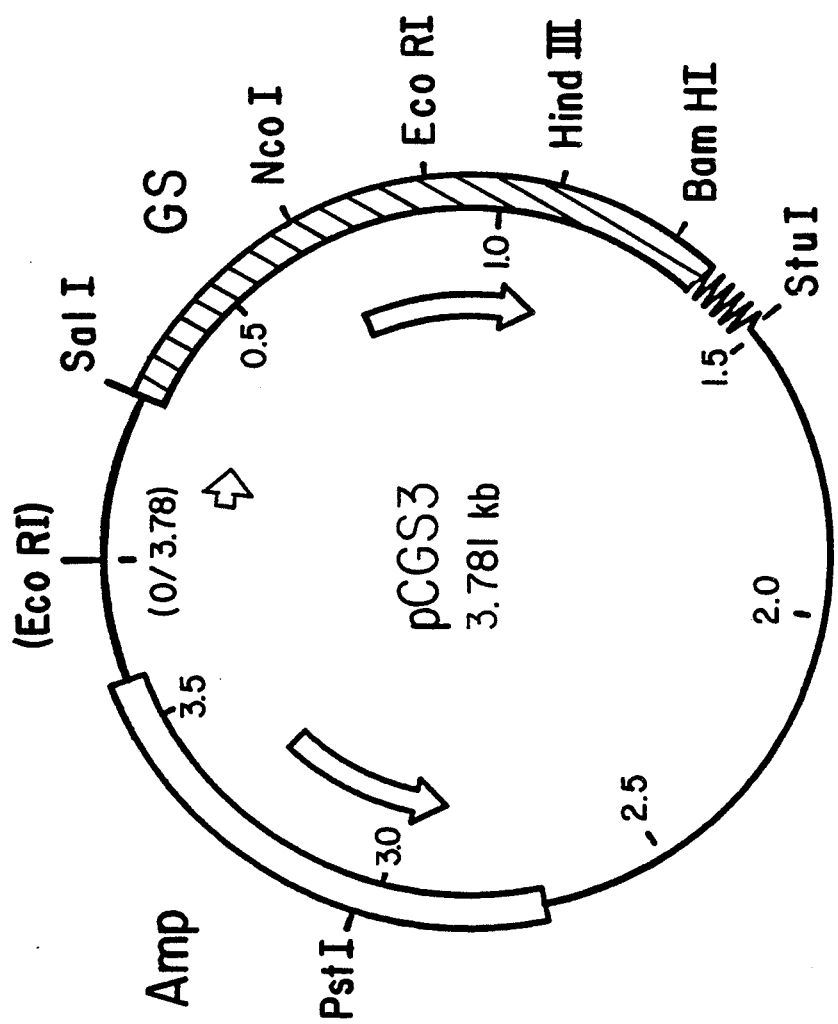
FIG. 4 shows a restriction map of pCGS3.

Plasmid pCGS3 was constructed from plasmid pCGS2 (see FIG. 1) by restriction at the EcoRI site, blunt end formation by fill-in at the site, religation and retransformation. pCGS3 therefore has only one EcoRI site and is missing the Eco RI site at position OKb in the plasmid. This is denoted as "(EcoRI)" in the plasmid map shown in FIG. 4.

C. Construction of Plasmid pCGS4

Figure 5:
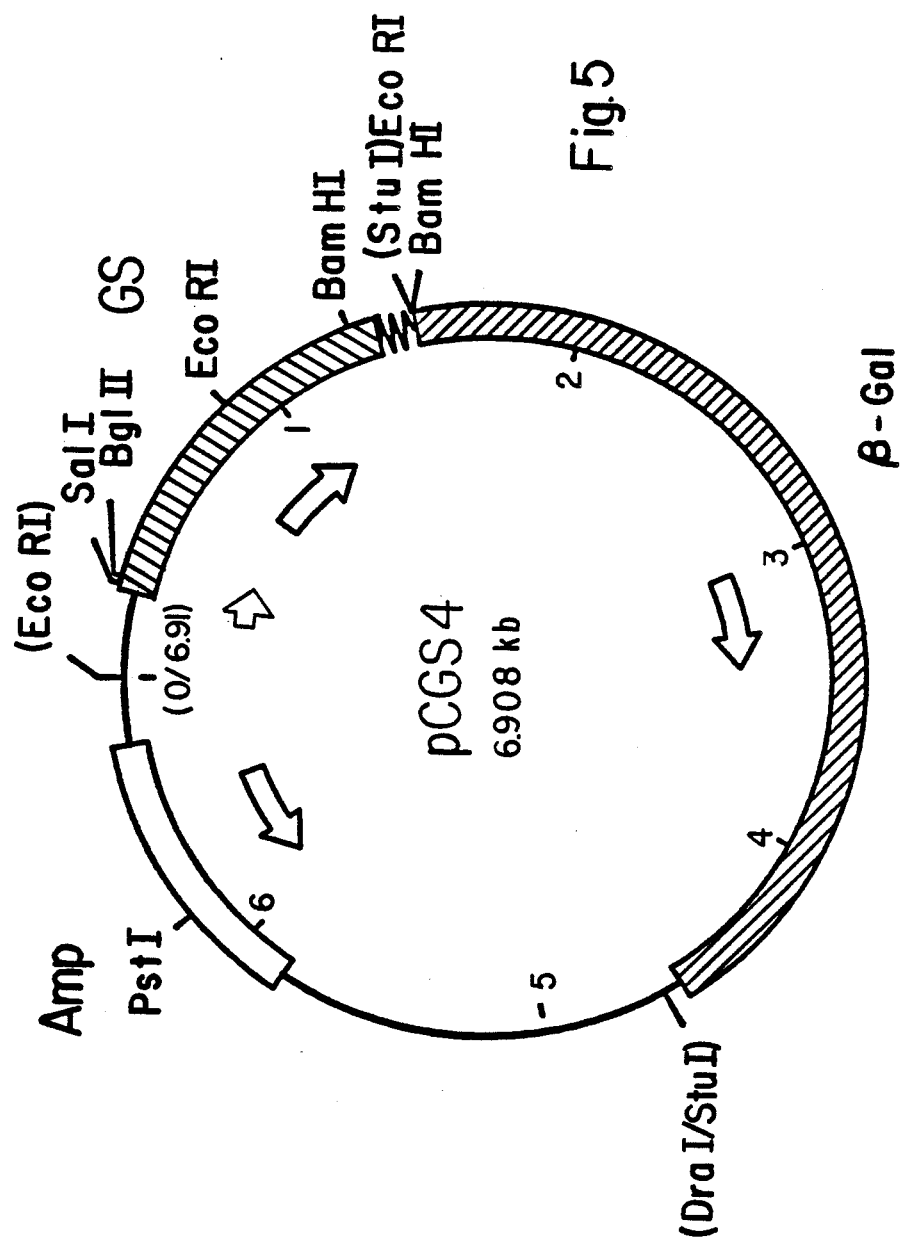
FIG. 5 shows a restriction map of pCGS4.

This plasmid was constructed from pCGS3 by restricting at the unique StuI site. The beta-galactosidase gene from pNRC 747 was cut out with a EcoRI and DraI digest. The EcoRI end was blunted, and the fragment was then blunt end ligated into the StuI site of pCGS3. After transformation of *E. coli*, plasmid pCGS4 with the right orientation (shown in FIG. 5) yielded blue colonies on IPTG-Xgal plates.

This construction using the beta-galactosidase gene was necessary in order to eliminate the majority (98%) of PPT resistant mutants which resulted when mutants were screened as described previously from overproduction of GS (i.e. due to plasmid copy number and/or up tac promoter mutants). Using pCGS4, those colonies that were PPT resistant and "light blue" (low levels of beta-galactosidase) presumably result from mutants other than overproduction, while those that are PPT resistant and "dark blue" (high levels of beta-galactosidase) are presumably due to overproduction.

D. Mutagenesis of pCGS4 with EMS.

This was carried out according to Conlonda and Miller, *J. Mol. Biol.* 525 (1977).

*E. coli* FDB213 (pCGS4) was grown overnight in M9PTA (M9 supplemented with L-proline, thiamine and 25 ug/ml ampicillin as indicated in *Advanced Bacterial Genetics* by Botstein, Davis et al.). Cells were spun down, washed twice with cold buffer (per liter 10.5 g $K_2HPO_4$, 4.5 g $KH_2PO_4$, 1 g $(NH_4)_2SO_4$ and 0.5 g sodium citrate dihydrate) and resuspended in one-half volume of buffer. The mutagen was added (0.07 x1 EMS per 5 ml of cells) and incubated for 45 minutes at 37° C. with shaking. Only 5% survived this treatment. After mutagenesis, the cells were spun down, washed with buffer twice, and resuspended in the same volume of buffer.

E. Selection for L-PPT Resistance

About $10^8$ cells (mutagenized) were plated on M9PT containing 5 mM L-PPT. About 1500 L-PPT resistant colonies were obtained. These were diluted with 1 liter LB and grown overnight. Plasmid DNA was purified from the culture and examined by agarose gel electrophoresis. A single band identical to pCGS4 was observed. The plasmid DNA was used to transform FDB213 and transformants plated on LB amp and M9PT (+5 mM L-PPT) plates. The number of transformants were equal on both plates.

F. Identification L-PPT Resistant GS Colony

To determine whether any of the plasmids contain a GS structural mutant, *E. coli* FDB213 was transformed and plated on M9PT plates with an overlay containing IPTG, X-gal and 5 mM L-PPT. Most colonies were dark blue with blue halos. Light blue colonies without halos were observed at about 2% frequency. Twenty-five light blue colonies were grown for two days in 1 ml of M9PT +5 mM L-PPT. Some colonies grew better than others. The cultures were diluted with 5 ml of LB and grown overnight. All cultures grew up to high density. These cultures (equal aliquots of the 25 individual cultures were pooled) all were diluted into 1 liter LB, grown, and plasmid DNA extracted. The about 1 kb SalI/BamHI fragment containing the alfalfa GS gene was gel purified and ligated into the SalI/BamHI backbone fragment of pCGS3. One clone resistant to 5 mM L-PPT was obtained.

G. Identification of the Gene Fragment Containing the Mutation

Fragment exchange was used to identify a restriction fragment containing the structural mutation in the GS gene. In this technique, the plasmid pCGS3 is cut with the following combinations of restriction enzymes: SalI - NcoI, NcoI - EcoRI, EcoRI - HindIII, and HindIII - BamHI (see Table I). The small insert was separated from the vector "backbone" by PAGE electrophoresis, and the vector backbone purified. The putative mutant pCGS4 plasmid was similarly cut and in this case the small insert gel-purified. The "mutant" insert was then ligated to the wild type "backbone," transformed into *E. coli*, and transformants selected for PPT resistance (see Table I). Tables I and II show the results obtained.

TABLE I

| LIGATIONS | | NUMBER OF COLONIES | | |
|---|---|---|---|---|
| INSERT | VECTOR | LB | M9 Amp | M9 AMP + 3 mM L-PPT |
| 1. None | SalI-NcoI | 41 | | |
| 2. PPT$^r$ SalI-NcoI | SalI-NcoI | 298 | | 8 |
| 3. None | NcoI-EcoRI | 26 | | |
| 4. PPT$^r$ NcoI-EcoRI | NcoI-EcoRI | 297 | | 6 |
| 5. None | EcoRI-HindIII | 9 | | |
| 6. PPT$^r$ EcoRI-HindIII | EcoRI-HindIII | 400 | | 300 |
| 7. None | HindIII-BamHI | 2 | | |
| 8. PPT$^r$ HindIII-BamHI | HindIII-BamHI | 74 | | 2 |
| 9. | CCC* pCGS3 | <1000 | >1000 | 100 |
| 10. | CCC pCGS3 PPT$^r$ | >1000 | >1000 | >1000 |

*covalently closed supercoiled plasmid DNA.

TABLE II

| | REPLATING | | | |
|---|---|---|---|---|
| Plasmid | M9 | M9/3 mM PPT | M9/6 mM PPT | M9/ 12 mM PPT |
| pCGS3 | LB +++ | + | 0 | 0 |
| | M9 +++ | + | 0 | 0 |
| pCGS3 PPT$^r$ | LB +++ | +++ | +++ | +++ |
| | M9 +++ | +++ | +++ | +++ |
| EcoRI-HindIII PPT$^r$ | LB +++ | +++ | +++ | +++ |
| | M9 +++ | +++ | +++ | +++ |

The EcoRI-HindIII fragment contains the structural mutation conferring PPT resistance.

H. Identification of the Specific Residue Involved

The EcoRI-HindIII fragment which encompasses amino acid residues 199-273, was sequenced and compared with the corresponding sequence of the wild type. The only change is replacement of a guanidine at position 733 by an adenine, resulting in replacement of glycine at position 245 by serine of that position.

*E. coli* FDB 213 (pCGS3-Ser 245) was deposited on Jan. 30, 1987 at the ATCC under the Budapest Treaty, and given accession number 67306.

EXAMPLE 4

Preparation of a PPT Resistanat GS Mutant, GS (LYS 332)

The experiments detailed in Example 3, A-F, were repeated exactly as described. Example 4G and H was repeated as in Example 3 with the exception of the results mentioned below.

Identification of the Gene Fragment Containing the Mutation

The result of the experiment in this Example 4 indicated the mutation was in the DNA fragment contained between the restriction enzyme cutting sites HindIII-BamHI (unlike Example 3 where the mutation was located in the DNA fragment between the EcoRI-HindIII sites; see Table I and II).

H. Identification of the Specific Residue Involved

The HindIII-BamHI fragment which encompasses amino acid residues 273-340, was sequenced and compared with the corresponding sequence of the wild-type gene. The only change is replacement of a guanidine at position 995 by an adenine, resulting in replacement of arginine (R) at position 332 by lysine (K) at that position.

I. Inhibition of Mutant and Wild-Type Glutamine Synthetase by PPT

Twenty-five ml cultures of *E. coli* FDB213 containing the wild-type GS expression plasmid, pCGS3, or the PPT resistant mutant plasmids of Example 3, pCGS-Ser245, or of Example 4, pCGS3-Lys332, were grown overnight at 37° C. in M9 media. The cells were collected by centrifugation at 5,000 r.p.m. (5° C.) for 5 min, resuspended in 1.0 ml 10mM Tris-HCl, pH 7.5, 1 mM EDTA, 5 mM beta-mercaptoethanol, and lysed by sonication. The lysates were clarified by centrifugation (5,000 r.p.m., 5° C., 5 min) and usually 100 ul of the supernatant assayed for GS enzyme activity and 5 ul for protein content. The specific activity of GS (units of GS activity/ug of protein) from pCGS3-Ser245-containing *E. coli* FDB213 was 2.2 times, and from pCGS3-Lys332-containing *E. coli* FDB213 was 1.7 times, the specific activity from wild-type pCGS3-containing *E. coli* FDB213. The GS activity in each of these extracts was also measured in the presence of 0, 4 uM, 25 uM, 62.5 uM, 125 uM, 250 uM, 2 mM, and 20 mM PPT. The results of this experiment are shown in Table III and FIG. 7.

TABLE III

| INHIBITION OF GS ACTIVITY BY PPT | | | |
|---|---|---|---|
| PPT Concen- | Relative GS Enzyme Activity | | |
| tration | pCGS3 | pCGS3-SER245 | pCGS3-LYS332 |
| 0 | 100% | 100% | 100% |

TABLE III-continued

| INHIBITION OF GS ACTIVITY BY PPT | | | |
|---|---|---|---|
| PPT Concen- | Relative GS Enzyme Activity | | |
| tration | pCGS3 | pCGS3-SER245 | pCGS3-LYS332 |
| 4 uM | 102% | 103% | 103% |
| 25 uM | 95.7% | 103% | 103% |
| 62.5 uM | 84.0% | 97.3% | 103% |
| 125 uM | 68.0% | 91.4% | 100% |
| 250 uM | 42.7% | 80.6% | 98.5% |
| 2 mM | 15.0% | 30.7% | 78.2% |
| 20 mM | 4.3% | 5.3% | 23.8% |

EXAMPLE 5

Isolation of a Leaf-Specific Glutamine Synthetase cDNA Clone from Arabidopsis Thaliana Total RNA was collected from *Arabidopsis thaliana* leaves, using the guanidinium/hot phenol method, and subjected to oligo-dT cellulose chromatography (Maniatis et al., *Molecular Cloning*, Cold Spring Harbor Laboratory, 1982). A cDNA library was constructed from the resulting leaf polyA+ RNA using the RNAse H method (Gubler et al., *Gene*, 25:263, 1983). The cDNA was cloned, using EcoRI linkers, into the EcoRI site of lambda gt11 (Young et al., *Proceedings of the National Academy of Science*, 80:1194, 1983). A leaf-specific Arabidopsis G cDNA clone, AtcGSL1, was isolated by immunoscreening this library according to the method of Huynh et al., in *DNA Cloning, a Practical Approach*, ed. D.M. Glover, IRL Press 1:49, 1985, with a specific polyclonal antibody raised against alfalfa glutamine synthetase (described in Example 2 above). The AtcGSL1 cDNA has the partial DNA sequence shown in FIG. 8.

AtcGS11 was used as radioactive probe in a Northern blot analysis. Arabidopsis leaf and root polyA+RNA (2 ug/lane) was electrophoresed on a glyoxal gel, blotted onto a nylon filter and uv-crosslinked (Church et al., *Proceedings of the National Academy of Science*, 81:1991, 1984). The blot (FIG. 9A) was hybridized with nick-translated EcoRI insert from AtcGSL1 using the conditions of Church et al., ibid. The results indicated that AtcGSL1 is preferentially expressed in leaves and that it represents a GS specific cDNA encoding a mRNA of approximately 1600 nucleotides in length.

Western blot analysis (Towbin et al., PNAS 76:4350, 1979) revealed that the leaf-specific GS polypeptide of Arabidopsis is light-inducible. Leaf and root proteins (50 ug/lane) were subjected to 10% SDS-polyacrylamide gel electrophoresis, blotted onto nitrocellulose paper, and probed with antibody to alfalfa GS followed by 125I-protein A. [Extract from alfalfa tissue culture cells containing an amplified GS gene (Dunn et al., *J. Mol. Appl. Genet.* 2:621, 1984) was included on this gel as a positive control (i.e., it was known to contain a GS polypeptide which specifically reacts with this antisera) and 39,000d molecular weight size marker.] The results indicated that Arabidopsis contains a 44,000d leaf-specific GS polypeptide. A 39,000d GS polypeptide is also present in both roots and leaves. In a Western blot (FIG. 10) of Arabidopsis seedlings grown in the dark, only the 39,000d GS polypeptide was detected. However, the 44,000d GS polypeptide reappeared, at levels comparable to those observed in light-grown plants, in dark-grown seedlings which were exposed to light and allowed to green.

EXAMPLE 6

Isolation of a Root-Specific GS cDNA Clone From Arabidopsis Thaliana

A root-specific Arabidopsis GS cDNA clone, AtcGSr1, was isolated from the lambda gt11 library described in Example 5 by antibody screening. A Northern blot (FIG. 9B) of Arabidopsis leaf and root polyA+ RNA probed with this clone indicated that AtcGsr1 is preferentially expressed in roots and that it represents a mRNA of approximately 1,400 nucleotides. AtcGsr1 has the partial DNA sequence shown in FIG. 11.

EXAMPLE 7

Isolation of a Root-Specific GS cDNA Clone From Arabidopsis Thaliana

A root-specific Arabidopsis GS cDNA clone, ATcGSr2, was isolated from the gt11 library described in Example 5 by antibody screening. A Northern blot (FIG. 9C) of Arabidopsis leaf and root polyA+ RNA initially probed with AtcGSL1 was stripped and reprobed with nick translated insert from AtcGSr2. The results indicated that AtcGSr2 is preferentially expressed in roots and that it represents a mRNA of approximately 1,400 nucleotides. (The upper band in the leaf RNA is due to residual hybridization of AtcGS11 to the larger leaf-specific GS mRNA.) AtcGSr2 has the partial DNA sequence shown in FIG. 12. The relative amounts of RNA corresponding to cDNA, AtcGSL1 in leaf, AtcGsr1 in root, and AtcGSr2 in root as roughly determined from the relative intensities of the bands on the Northern blot in FIG. 9 and the relative exposure times of parts A, B, and C of that blot are 15:1:1 respectively.

It is understood that these descriptions, examples and embodiments are for illustrative purposes only, and that various modifications will be suggested within the spirit and purview of this application and the scope of the appended claims.

We claim:

1. A mutant alfalfa glutamine synthetase enzyme which is resistant to inhibition by a herbicidal glutamine synthetase inhibitor.

2. A mutant alfalfa glutamine synthetase enzyme which is resistant to inhibition by a herbicidal glutamine synthetase inhibitor wherein said glutamine synthetase enzyme has the following amino acid sequence:

| 1 | M | S | L | L | S | D | L | I | N | L | D | L | S | E | T | T | E | K | I | I |
|---|---|---|---|---|---|---|---|---|---|---|---|---|---|---|---|---|---|---|---|---|
| 21 | A | E | Y | I | W | I | G | G | S | G | L | D | L | R | S | K | A | R | T | L |
| 41 | P | G | P | V | T | D | P | S | Q | L | P | K | W | N | Y | D | G | S | S | T |
| 61 | G | Q | A | P | G | E | D | S | E | V | I | I | Y | P | Q | A | I | F | K | D |
| 81 | P | F | R | R | G | N | N | I | L | V | M | C | D | A | Y | T | P | A | G | E |
| 101 | P | I | P | T | N | K | R | H | A | A | A | K | I | F | S | H | P | D | V | V |
| 121 | A | E | V | P | W | Y | G | I | E | Q | E | Y | T | L | L | Q | K | D | I | N |
| 141 | W | P | L | G | W | P | V | G | G | F | P | G | P | Q | G | P | Y | Y | C | G |
| 161 | A | G | A | D | K | A | F | G | R | D | I | V | D | S | H | Y | K | A | C | L |
| 181 | Y | A | G | I | N | I | S | G | I | N | G | E | V | M | P | G | Q | W | E | F |
| 201 | Q | V | G | P | S | V | $X^1$ | I | S | A | G | D | E | I | W | V | A | R | Y | I |
| 221 | L | E | R | I | T | E | V | A | G | V | V | L | S | F | D | P | K | P | I | K |
| 241 | G | D | W | N | $X^2$ | A | G | A | H | T | N | Y | S | T | K | S | M | R | E | D |
| 261 | G | G | Y | E | V | I | L | K | A | I | E | K | L | G | K | K | H | K | E | H |
| 281 | I | A | A | Y | G | E | G | N | E | R | R | L | T | G | R | H | E | T | A | D |
| 301 | I | N | T | F | L | W | G | V | A | N | R | G | A | S | I | R | V | G | R | D |
| 321 | T | E | K | A | G | K | G | Y | F | E | D | $X^3$ | R | P | S | S | N | M | D | P |
| 341 | Y | V | V | T | S | M | I | A | D | T | T | I | L | W | K | P | | | | | where $x^1$ at 207 is G;

$X^2$ at 245 represents an amino acid other than glycine; and $X^3$ at 332 is arginine or lysine.

3. The mutant alfalfa glutamine synthetase of claim 2 wherein said $X^2$ is neutral or basic.

4. The mutant alfalfa glutamine synthetase of claim 2 wherein said $X_2$ is selected from the group consisting of serine, arginine, and cysteine.

5. The mutant alfalfa glutamine synthetase of claim 2, wherein said $X^3$ is lysine.

6. A mutant alfalfa glutamine synthetase enzyme which is resistant to inhibition by a herbicidal glutamine synthetase inhibitor, wherein said enzyme lacks the four native N-terminal amino acid residues 2 to 5, inclusive.

7. A mutant alfalfa glutamine synthetase enzyme which is resistant to inhibition by a herbicidal glutamine synthetase inhibitor, wherein said enzyme has the formula:

| 1 | M | S | L | L | S | D | L | I | N | L | D | L | S | E | T | T | E | K | I | I |
|---|---|---|---|---|---|---|---|---|---|---|---|---|---|---|---|---|---|---|---|---|
| 21 | A | E | Y | I | W | I | G | G | S | G | L | D | L | R | S | K | A | R | T | L |
| 41 | P | G | P | V | T | D | P | S | Q | L | P | K | W | N | Y | D | G | S | S | T |
| 61 | G | Q | A | P | G | E | D | S | E | V | I | I | Y | P | Q | A | I | F | K | D |
| 81 | P | F | R | R | G | N | N | I | L | V | M | C | D | A | Y | T | P | A | G | E |
| 101 | P | I | P | T | N | K | R | H | A | A | A | K | I | F | S | H | P | D | V | V |
| 121 | A | E | V | P | W | Y | G | I | E | Q | E | Y | T | L | L | Q | K | D | I | N |
| 141 | W | P | L | G | W | P | V | G | G | F | P | G | P | Q | G | P | Y | Y | C | G |
| 161 | A | G | A | D | K | A | F | G | R | D | I | V | D | S | H | Y | K | A | C | L |
| 181 | Y | A | G | I | N | I | S | G | I | N | G | E | V | M | P | G | Q | W | E | F |
| 201 | Q | V | G | P | S | V | $X^1$ | I | S | A | G | D | E | I | W | V | A | R | Y | I |
| 221 | L | E | R | I | T | E | V | A | G | V | V | L | S | F | D | P | K | P | I | K |
| 241 | G | D | W | N | $X^2$ | A | G | A | H | T | N | Y | S | T | K | S | M | R | E | D |
| 261 | G | G | Y | E | V | I | L | K | A | I | E | K | L | G | K | K | H | K | E | H |
| 281 | I | A | A | Y | G | E | G | N | E | R | R | L | T | G | R | H | E | T | A | D |
| 301 | I | N | T | F | L | W | G | V | A | N | R | G | A | S | I | R | V | G | R | D |
| 321 | T | E | K | A | G | K | G | Y | F | E | D | $X^3$ | R | P | S | S | N | M | D | P |

-continued

| 341 | Y | V | V | T | S | M | I | A | D | T | T | I | L | W | K | P | where X¹ at 207 is G;
X² at 245 represents an amino acid other than glycine; and
X³ at 332 is lysine; and wherein said enzyme lacks the four native N-terminal amino acid residues 2 to 5, inclusive.

8. A mutant alfalfa glutamine synthetase enzyme having the following amino acid sequence:

X³ at 332 is arginine or lysine; and
wherein said amino acid sequence lacks the methionine residue at position 1.

9. The glutamine synthetase of claim 1, wherein said inhibitor is phosphinothricin.

10. A nucleic acid molecule coding for a mutant alfalfa glutamine synthetase enzyme which is resistant to inhibition by a herbicidal glutamine synthetase inhibitor.

| 1 | M | S | L | L | S | D | L | I | N | L | D | L | S | E | T | T | E | K | I | I |
| 21 | A | E | Y | I | W | I | G | G | S | G | L | D | L | R | S | K | A | R | T | L |
| 41 | P | G | P | V | T | D | P | S | Q | L | P | K | W | N | Y | D | G | S | S | T |
| 61 | G | Q | A | P | G | E | D | S | E | V | I | I | Y | P | Q | A | I | F | K | D |
| 81 | P | F | R | R | G | N | N | I | L | V | M | C | D | A | Y | T | P | A | G | E |
| 101 | P | I | P | T | N | K | R | H | A | A | A | K | I | F | S | H | P | D | V | V |
| 121 | A | E | V | P | W | Y | G | I | E | Q | E | Y | T | L | L | Q | K | D | I | N |
| 141 | W | P | L | G | W | P | V | G | G | F | P | G | P | Q | G | P | Y | Y | C | G |
| 161 | A | G | A | D | K | A | F | G | R | D | I | V | D | S | H | Y | K | A | C | L |
| 181 | Y | A | G | I | N | I | S | G | I | N | G | E | V | M | P | G | Q | W | E | F |
| 201 | Q | V | G | P | S | V | X¹ | I | S | A | G | D | E | I | W | V | A | R | Y | I |
| 221 | L | E | R | I | T | E | V | A | G | V | V | L | S | F | D | P | K | P | I | K |
| 241 | G | D | W | N | X² | A | G | A | H | T | N | Y | S | T | K | S | M | R | E | D |
| 261 | G | G | Y | E | V | I | L | K | A | I | E | K | L | G | K | K | H | K | E | H |
| 281 | I | A | A | Y | G | E | G | N | E | R | R | L | T | G | R | H | E | T | A | D |
| 301 | I | N | T | F | L | W | G | V | A | N | R | G | A | S | I | R | V | G | R | D |
| 321 | T | E | K | A | G | K | G | Y | F | E | D | X³ | R | P | S | S | N | M | D | P |
| 341 | Y | V | V | T | S | M | I | A | D | T | T | I | L | W | K | P | where X¹ at 207 is G;
X² at 245 represents an amino acid other than glycine;

tor.

11. The nucleic acid molecule of claim 10, which is the following:

```
  1 ATGTCTCTCCTTTCAGATCTTATCAACCTTGACCTCTCCGAAACCACCGAGAAAATCATC

61 GCCGAATACATATGGATTGGTGGATCTGGTTTGGACTTGAGGAGCAAAGCAAGGACTCTA

121 CCAGGACCAGTTACTGACCCTTCACAGCTTCCCAAGTGGAACTATGATGGTTCCAGCACA

181 GGTCAAGCTCCTGGAGAAGATAGTGAAGTTATTATCTACCCACAAGCCATTTTCAAGGAC

241 CCATTTAGAAGGGGTAACAATATCTTGGTTATGTGTGATGCATACACTCCAGCTGGAGAG

301 CCCATTCCCACCAACAAGAGACATGCAGCTGCCAAGATTTTCAGCCATCCTGATGTTGTT

361 GCTGAAGTACCATGGTATGGTATTGAGCAAGAATACACCTTGTTGCAGAAAGACATCAAT

421 TGGCCTCTTGGTTGGCCAGTTGGTGGTTTTCCTGGACCTCAGGGACCATACTATTGTGGA

481 GCTGGTGCTGACAAGGCATTTGGCCGTGACATTCTTGACTCACATTACAAAGCCTGTCTT

541 TATGCCGGCATCAACATCAGTGGAATCAATGGTGAAGTGATGCCTGGTCAATGGGAATTC

601 CAAGTTGGTCCCTCAX⁴GGTATCTCTGCTGGTGATGAGATATGGGTTGCTCGTTACATT

661 TTGGAGAGGATCACTGAGGTTGCTGGTGTGGTGCTTTCCTTTGACCCAAAACCAATTAAG

721 GGTGATTGGAATX⁵GCTGGTGCTCACACAAATTACAGCACCAAGTCGATGAGAGAAGAT

781 GGTGGCTATGAAGTCATCTTGAAAGCAATTGAGAAGCTTGGGAAGAAGCACAAGGAGCAC

841 ATTGCTGCTTATGGAGAAGGCAACGAGCGTAGATTGACAGGGCGACATGAGACAGCTGAC
```

-continued

```
901  ATTAACACCTTCTTATGGGGTGTTGCAAACCGTGGTGCGTCGATTAGAGTTGGAAGGGAC

961  ACAGAGAAAGCAGGGAAAGGTTATTTCGAGGATX⁶AGGCCATCATCTAACATGGATCCA

1021 TATGTTGTTACTTCCATGATTGCAGACACCACCATTCTCTGGAAACCA
``` wherein X⁴ is a triplet which codes for gly;
X⁵ is a triplet which codes for an amino acid other than glycine; and
X⁶ is a triplet which codes for arginine or lysine.

12. The nucleic acid molecule of claim 11, wherein said amino acid encoded by X⁵ is neutral or basic.

13. The nucleic acid molecule of claim 11, wherein said amino acid encoded by X⁵ is selected from the group consisting of serine, arginine, or cysteine.

14. The nucleic acid molecule of claim 11, wherein said X⁶ is a triplet which codes for lysine.

15. A nucleic acid molecule coding for a mutant alfalfa glutamine synthetase enzyme which is resistant to inhibition by a herbicidal glutamine synthetase inhibitor, wherein said nucleic acid sequence further comprises an ATG codon prior to the codon for the first N-terminal amino acid residue.

16. The nucleic acid molecule of claim 10, wherein said inhibitor is phosphinothricin.

17. A recombinant DNA molecule comprising a nucleotide sequence coding for a mutant alfalfa glutamine synthetase enzyme which is resistant to inhibition by a herbicidal glutamine synthetase inhibitor.

18. The recombinant DNA molecule of claim 17, which is a plasmid.

19. The recombinant DNA molecule of claim 18, wherein said nucleotide sequence is in operable linkage and expressible by a prokaryotic promoter, and further comprising a prokaryotic origin of replication, wherein when a prokaryote is transformed with said plasmid, said plasmid replicates.

20. The plasmid of claim 19, which is the Ti plasmid of *Agrobacterium tumefaciens*.

21. The recombinant DNA molecule of claim 19, wherein said nucleotide sequence is in further operable linkage with and expressible by a transcription promoter for the expression of said glutamine synthetase sequence in a plant cell.

22. A host cell transformed by the recombinant DNA molecule of claim 17.

23. The host cell of claim 22 which is a prokaryotic microorganism.

24. The host cell of claim 22, which is a plant cell.

25. A plasmid comprising a prokaryotic origin of replication, a prokaryotic promoter, and a nucleotide sequence coding for a mutant alfalfa glutamine synthetase enzyme which is resistant to inhibition by a herbicidal glutamine synthetase inhibitor, wherein when a prokaryotic host is transformed with said plasmid, said plasmid replicates and said enzyme is expressible.

26. A prokaryotic transformed with a recombinant DNA molecule comprising a nucleotide sequence coding for a mutant alfalfa glutamine synthetase enzyme which is resistant to inhibition by a herbicidal glutamine synthetase inhibitor.

27. The prokaryotic of claim 26, wherein said recombinant DNA molecule is a plasmid.

28. The prokaryotic of claim 27, which is a bacterium which, in its untransformed state, is incapable of producing the functional wildtype bacterial glutamine synthetase.

29. The prokaryotic of claim 28, which is a mutant bacterium which, in its untransformed state, exhibits diminished glutamine synthetase activity in comparison to the wild type bacterium.

30. The prokaryotic as in any of claims 26, 28 or 29, which is *E. coli*.

* * * * *

UNITED STATES PATENT AND TRADEMARK OFFICE
CERTIFICATE OF CORRECTION

PATENT NO. : 4,975,374

DATED : December 4, 1990

INVENTOR(S) : Howard Goodman, Shiladitya DasSarma, Edmund Tischer, Theresa K. Peterman It is certified that error appears in the above-identified patent and that said Letters Patent is hereby corrected as shown below:

The cover page of the patent should be amended to reflect the following:

--[63]  Related U.S. Appln. Data: Continuation-In-Part of Serial No. 906,984, September 15, 1986, abandoned, and a continuation-in-part of 840,744, March 18, 1986, abandoned.--

Signed and Sealed this

Twenty-third Day of June, 1992

Attest:

DOUGLAS B. COMER

Attesting Officer

Acting Commissioner of Patents and Trademarks